US012735774B2

(12) United States Patent
Manley et al.

(10) Patent No.: US 12,735,774 B2
(45) Date of Patent: Sep. 15, 2026

(54) PROCESSING OF COBALT-TUNGSTEN ALLOYS

(71) Applicant: Abbott Cardiovascular Systems, Inc., Santa Clara, CA (US)

(72) Inventors: Donal F. Manley, Cork (IE); Puneet Kamal Singh Gill, Anaheim, CA (US); Diarmuid P. Meagher, Golden (IE)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 579 days.

(21) Appl. No.: 18/324,749

(22) Filed: May 26, 2023

(65) Prior Publication Data

US 2023/0399725 A1 Dec. 14, 2023

Related U.S. Application Data

(60) Provisional application No. 63/350,106, filed on Jun. 8, 2022.

(51) Int. Cl.
*C22C 30/00* (2006.01)
*A61F 2/82* (2013.01)

(52) U.S. Cl.
CPC ................ *C22C 30/00* (2013.01); *A61F 2/82* (2013.01); *A61F 2310/00035* (2013.01)

(58) Field of Classification Search
CPC . C22C 19/07; C22C 30/00; C22F 1/10; C22F 1/11; C22F 1/14
See application file for complete search history.

(56) References Cited

U.S. PATENT DOCUMENTS

| | | | |
|---|---|---|---|
| 2,938,850 | A | 5/1960 | Hans |
| 3,203,884 | A | 8/1965 | Heinz et al. |
| 3,612,058 | A | 10/1971 | Ackerman |
| 3,635,703 | A | 1/1972 | Pissarevsky |
| 3,912,550 | A | 10/1975 | Bolte et al. |
| 3,937,628 | A | 2/1976 | Watanabe et al. |
| 4,127,459 | A | 11/1978 | Jumer |
| 4,330,381 | A | 5/1982 | Jumer |
| 4,654,092 | A | 3/1987 | Melton |
| 4,685,977 | A | 8/1987 | Chang |
| 4,846,186 | A | 7/1989 | Box et al. |
| 4,854,330 | A | 8/1989 | Evans et al. |
| 4,967,753 | A | 11/1990 | Haase et al. |
| 5,061,275 | A | 10/1991 | Wallsten et al. |
| 5,067,489 | A | 11/1991 | Lind |
| 5,069,226 | A | 12/1991 | Yamauchi et al. |
| 5,147,317 | A | 9/1992 | Shank et al. |
| 5,171,383 | A | 12/1992 | Sagae et al. |
| 5,174,295 | A | 12/1992 | Christian et al. |
| 5,174,302 | A | 12/1992 | Palmer |
| 5,184,621 | A | 2/1993 | Vogel et al. |
| 5,238,004 | A | 8/1993 | Sahatjian et al. |
| 5,287,858 | A | 2/1994 | Hammerslag et al. |
| 5,330,826 | A | 7/1994 | Taylor et al. |
| 5,353,798 | A | 10/1994 | Sieben |
| 5,353,808 | A | 10/1994 | Viera |
| 5,354,623 | A | 10/1994 | Hall |
| 5,404,887 | A | 4/1995 | Prather |
| 5,421,955 | A | 6/1995 | Lau et al. |
| 5,433,200 | A | 7/1995 | Fleischhacker, Jr. |
| 5,449,369 | A | 9/1995 | Imran |
| 5,480,382 | A | 1/1996 | Hammerslag et al. |
| 5,514,154 | A | 5/1996 | Lau et al. |
| 5,569,295 | A | 10/1996 | Lam |
| 5,603,721 | A | 2/1997 | Lau et al. |
| 5,618,299 | A | 4/1997 | Khosravi et al. |
| 5,628,787 | A | 5/1997 | Mayer |
| 5,630,840 | A | 5/1997 | Mayer |
| 5,636,641 | A | 6/1997 | Fariabi |

(Continued)

FOREIGN PATENT DOCUMENTS

| | | | |
|---|---|---|---|
| CN | 101115869 | A | 1/2008 |
| CN | 101554685 | A | 10/2009 |

(Continued)

OTHER PUBLICATIONS

Luty, Wacław. "Types of cooling media and their properties." Theory and technology of quenching: a handbook. Berlin, Heidelberg: Springer Berlin Heidelberg, 1992. 248-340.*

(Continued)

*Primary Examiner* — Jessee R Roe
(74) *Attorney, Agent, or Firm* — Workman Nydegger

(57) ABSTRACT

Radiopaque implantable structures (e.g., stents) formed of cobalt-based alloys that comprise cobalt, chromium, tungsten, nickel, and platinum or another another metal having an atomic number or density greater than that of cobalt for increased radiopacity. In particular, processes are described for removing precipitate inclusions (e.g., tungsten rich precipitates) that render the alloy otherwise unsuitable for use in formation of a stent or similar implantable structure. The alloy with such precipitate inclusions can be heat treated within a narrow temperature range of about 1250° C. (e.g., 1225° C. to 1275° C.) for a time period in a narrow range of about 30 minutes (e.g., 20 to 40 minutes), to remove such precipitate inclusions. Higher temperatures and/or longer treatment times surprisingly do not resolve the precipitate inclusions, but treatment at about 1250° C. for about 30 minutes substantially removes the precipitates, resulting in a substantially homogenous structure suitable for use as a stent.

20 Claims, 10 Drawing Sheets

(56) References Cited

U.S. PATENT DOCUMENTS 5,649,952 A 7/1997 Lam
5,666,969 A 9/1997 Urick et al.
5,673,707 A 10/1997 Chandrasekaran
5,695,111 A 12/1997 Nanis
5,716,400 A 2/1998 Davidson
5,716,417 A 2/1998 Girard et al.
5,725,572 A 3/1998 Lam et al.
5,728,158 A 3/1998 Lau et al.
5,735,893 A 4/1998 Lau et al.
5,746,701 A 5/1998 Noone
5,759,192 A 6/1998 Saunders
5,766,238 A 6/1998 Lau et al.
5,776,080 A 7/1998 Thome et al.
5,788,654 A 8/1998 Schwager
5,797,857 A 8/1998 Obitsu
5,799,386 A 9/1998 Ingersoll et al.
5,803,344 A 9/1998 Stankavich et al.
5,824,077 A 10/1998 Mayer
5,849,037 A 12/1998 Frid
5,858,556 A 1/1999 Eckert et al.
5,865,767 A 2/1999 Frechette et al.
5,876,432 A 3/1999 Lau et al.
5,891,055 A 4/1999 Sauter
5,891,191 A 4/1999 Stinson
5,916,178 A 6/1999 Noone et al.
5,984,973 A 11/1999 Girard et al.
5,985,126 A 11/1999 Bleck et al.
6,004,279 A 12/1999 Crowley et al.
6,027,528 A 2/2000 Tomonto et al.
6,139,511 A 10/2000 Huter et al.
6,183,353 B1 2/2001 Frantzen
6,214,200 B1 4/2001 Altena et al.
6,221,096 B1 4/2001 Aiba et al.
6,234,981 B1 5/2001 Howland
6,287,331 B1 9/2001 Heath
6,355,058 B1 3/2002 Pacetti et al.
6,375,826 B1 4/2002 Wang et al.
6,390,992 B1 5/2002 Morris et al.
6,419,693 B1 7/2002 Fariabi
6,500,130 B2 12/2002 Kinsella et al.
6,503,290 B1 1/2003 Jarosinski et al.
6,508,803 B1 1/2003 Horikawa et al.
6,592,570 B2 7/2003 Abrams et al.
6,599,415 B1 7/2003 Ku et al.
6,602,228 B2 8/2003 Nanis et al.
6,602,272 B2 8/2003 Boylan et al.
6,610,046 B1 8/2003 Usami et al.
6,620,192 B1 9/2003 Jalisi
6,679,980 B1 1/2004 Andreacchi
7,105,018 B1 9/2006 Yip et al.
7,156,869 B1 1/2007 Pacetti
7,208,070 B2 4/2007 Swain
7,244,319 B2 7/2007 Abrams et al.
7,250,058 B1 7/2007 Pacetti et al.
7,252,746 B2 8/2007 Schaeffer
7,294,214 B2 11/2007 Craig
7,318,837 B2 1/2008 Krivoruchko et al.
7,357,854 B1 4/2008 Andreacchi
7,413,574 B2 8/2008 Yip et al.
7,488,343 B2 2/2009 O'Brien et al.
7,494,474 B2 2/2009 Richardson et al.
7,498,062 B2 3/2009 Calcaterra et al.
7,501,048 B2 3/2009 Loermans et al.
7,540,997 B2 6/2009 Stinson
7,601,230 B2 10/2009 Craig
7,632,303 B1 12/2009 Stalker et al.
7,740,798 B2 6/2010 Stinson
7,771,581 B2 8/2010 Callol et al.
7,776,189 B2 8/2010 Shrivastava et al.
7,785,274 B2 8/2010 Mishima et al.
7,883,474 B1 2/2011 Mirigian et al.
8,100,837 B1 1/2012 Cornish et al.
8,267,872 B2 9/2012 Ressemann et al.
8,323,459 B2 12/2012 Andreacchi et al.
8,348,860 B2 1/2013 Murayama et al.
8,360,995 B2 1/2013 Elsesser et al.
8,430,923 B2 4/2013 Pacetti et al.
8,529,710 B2 9/2013 Ishida et al.
8,591,672 B2 11/2013 Janko et al.
8,613,849 B2 12/2013 Wong et al.
8,617,379 B2 12/2013 Wong et al.
8,617,380 B2 12/2013 Wong et al.
8,790,393 B2 7/2014 Bregulla et al.
8,808,618 B2 8/2014 Furst et al.
8,815,061 B2 8/2014 Andreacchi et al.
8,852,264 B2 10/2014 Pacetti et al.
8,992,761 B2 3/2015 Lin
9,045,843 B2 6/2015 Andreacchi et al.
9,133,563 B2 9/2015 Andreacchi
9,145,619 B2 9/2015 Andreacchi et al.
9,566,147 B2 2/2017 Kramer-Brown et al.
9,566,174 B1 2/2017 De et al.
9,592,135 B2 3/2017 Thompson
9,668,890 B2 6/2017 Ma et al.
9,724,494 B2 8/2017 Purtzer
10,441,445 B2 10/2019 Kramer-Brown et al.
10,617,541 B2 4/2020 Nishigishi
10,835,393 B2 11/2020 Ma et al.
11,141,296 B2 10/2021 Thompson
11,298,251 B2 4/2022 Simpson et al.
11,779,477 B2 10/2023 Simpson et al.
11,806,488 B2 11/2023 Purtzer
12,150,872 B2 11/2024 Simpson et al.
12,151,049 B2 11/2024 Simpson et al.
2001/0009981 A1 7/2001 Dubois et al.
2002/0032477 A1 3/2002 Helmus et al.
2002/0062092 A1 5/2002 Muni et al.
2002/0082524 A1 6/2002 Anderson et al.
2002/0087099 A1 7/2002 Nanis et al.
2003/0102360 A1 6/2003 Eungard et al.
2003/0120181 A1 6/2003 Toma et al.
2003/0125642 A1 7/2003 Kato et al.
2003/0134142 A1 7/2003 Ivey et al.
2004/0111044 A1 6/2004 Davis et al.
2004/0129347 A1 7/2004 Craig
2004/0167436 A1 8/2004 Reynolds et al.
2004/0167442 A1 8/2004 Shireman et al.
2004/0181175 A1 9/2004 Clayman et al.
2004/0225231 A1 11/2004 Ehr
2004/0236433 A1 11/2004 Kennedy et al.
2004/0243168 A1 12/2004 Ferrera et al.
2004/0267351 A1 12/2004 Swain
2005/0054952 A1 3/2005 Eskuri et al.
2005/0056687 A1 3/2005 Matsumoto et al.
2005/0059889 A1 3/2005 Mayer
2005/0060025 A1 3/2005 Mackiewicz et al.
2005/0070997 A1 3/2005 Thornton et al.
2005/0096568 A1 5/2005 Kato
2005/0098444 A1 5/2005 Schaeffer
2005/0124917 A1 6/2005 Skujins et al.
2005/0137501 A1 6/2005 Euteneuer et al.
2005/0145307 A1 7/2005 Shireman et al.
2005/0145508 A1 7/2005 Larsen et al.
2005/0263171 A1 12/2005 Wu et al.
2005/0263717 A1 12/2005 Soluri et al.
2005/0267385 A1 12/2005 Hofmann et al.
2005/0273021 A1 12/2005 Burgermeister
2005/0273156 A1 12/2005 Burgermeister et al.
2005/0288773 A1 12/2005 Glocker et al.
2006/0079954 A1 4/2006 Burgermeister et al.
2006/0122537 A1 6/2006 Reynolds et al.
2006/0190070 A1 8/2006 Dieck et al.
2006/0241519 A1 10/2006 Hojeibane et al.
2006/0259126 A1 11/2006 Lenz
2006/0264784 A1 11/2006 Lupton
2006/0271169 A1 11/2006 Lye et al.
2006/0272751 A1 12/2006 Kato
2006/0287709 A1 12/2006 Rao
2007/0034527 A1 2/2007 Diaz et al.
2007/0034528 A1 2/2007 Diaz et al.
2007/0135891 A1 6/2007 Schneider
2007/0156215 A1 7/2007 Jensen et al.
2007/0173925 A1 7/2007 Fliedner
2007/0185415 A1 8/2007 Ressemann et al.

(56) References Cited

U.S. PATENT DOCUMENTS

2007/0185564 A1 8/2007 Pacetti et al.
2007/0198044 A1 8/2007 Lupton et al.
2007/0209947 A1 9/2007 Shrivastava et al.
2007/0219464 A1 9/2007 Davis et al.
2007/0219465 A1 9/2007 Cedro et al.
2007/0219624 A1 9/2007 Brown et al.
2007/0244413 A1 10/2007 Biggins
2007/0249964 A1 10/2007 Richardson et al.
2007/0249965 A1 10/2007 Abrams et al.
2007/0265699 A1 11/2007 Grewe et al.
2007/0270942 A1 11/2007 Thomas
2008/0004546 A1 1/2008 Kato
2008/0033522 A1 2/2008 Grewe et al.
2008/0070058 A1 3/2008 Dasgupta et al.
2008/0077049 A1 3/2008 Hirshman
2008/0091267 A1 4/2008 Stinson et al.
2008/0097248 A1 4/2008 Munoz et al.
2008/0146967 A1 6/2008 Richardson et al.
2008/0160259 A1 7/2008 Nielson et al.
2008/0161726 A1 7/2008 Itou
2008/0177371 A1 7/2008 Ryan et al.
2008/0183280 A1 7/2008 Agnew et al.
2008/0200879 A1 8/2008 Jalisi et al.
2008/0208308 A1 8/2008 Allen et al.
2008/0208352 A1 8/2008 Krivoruchko et al.
2008/0215132 A1 9/2008 Ryan et al.
2008/0228109 A1 9/2008 Kinoshita et al.
2008/0234605 A1 9/2008 Urie
2008/0257717 A1 10/2008 Vacheron
2008/0262600 A1 10/2008 Jalisi
2008/0281230 A1 11/2008 Kinoshita et al.
2008/0312747 A1 12/2008 Cameron et al.
2009/0000105 A1 1/2009 Kato
2009/0030500 A1 1/2009 Weber et al.
2009/0048659 A1 2/2009 Weber et al.
2009/0093871 A1 4/2009 Rea et al.
2009/0112127 A1 4/2009 Keating et al.
2009/0118675 A1 5/2009 Czyscon et al.
2009/0118822 A1 5/2009 Holman et al.
2009/0149947 A1 6/2009 Frohwitter
2009/0163833 A1 6/2009 Kinoshita et al.
2009/0204203 A1 8/2009 Allen et al.
2009/0227902 A1 9/2009 Simpson et al.
2009/0240324 A1 9/2009 Smith
2009/0254000 A1 10/2009 Layman et al.
2009/0255827 A1 10/2009 Andreacchi et al.
2009/0258050 A1 10/2009 Lindsay et al.
2009/0259299 A1 10/2009 Moloney
2009/0276033 A1 11/2009 Mayer
2010/0004562 A1 1/2010 Jalisi et al.
2010/0004733 A1 1/2010 Atanasoska et al.
2010/0049304 A1 2/2010 Clifford et al.
2010/0158426 A1 6/2010 Manipatruni et al.
2010/0158436 A1 6/2010 Riska
2010/0172789 A1 7/2010 Calla et al.
2010/0217373 A1 8/2010 Boyle et al.
2010/0222866 A1 9/2010 Wachter et al.
2010/0222873 A1 9/2010 Atanasoska et al.
2010/0241210 A1 9/2010 Patadia
2010/0249654 A1 9/2010 Elsesser et al.
2010/0262227 A1 10/2010 Rangwala et al.
2011/0062031 A1 3/2011 Wulf
2011/0066106 A1 3/2011 Kato
2011/0098648 A1 4/2011 Kato
2011/0106236 A1 5/2011 Su et al.
2011/0118628 A1 5/2011 Zhou et al.
2011/0247943 A1 10/2011 Bialas et al.
2011/0264161 A1 10/2011 Schiefer et al.
2011/0319872 A1 12/2011 Kawasaki
2011/0319980 A1 12/2011 Ryan
2012/0016458 A1 1/2012 Abunassar
2012/0041342 A1 2/2012 Purtzer
2012/0065623 A1 3/2012 Nelson et al.
2012/0109108 A1 5/2012 Boyle et al.
2012/0123525 A1 5/2012 Kramer-Brown et al.
2012/0199489 A1 8/2012 Vacheron
2012/0282571 A1 11/2012 Ammon et al.
2013/0006149 A1 1/2013 Purtzer
2013/0006222 A1 1/2013 Nabeshima et al.
2013/0013055 A1 1/2013 Pacetti et al.
2013/0092554 A1 4/2013 Wong et al.
2013/0092556 A1 4/2013 Wong et al.
2013/0092557 A1 4/2013 Wong et al.
2013/0096669 A1 4/2013 Bregulla et al.
2013/0204353 A1 8/2013 Kramer-Brown et al.
2013/0241112 A1 9/2013 Jow
2014/0014530 A1 1/2014 Lin
2014/0076719 A1 3/2014 Andreacchi et al.
2014/0076720 A1 3/2014 Andreacchi et al.
2014/0076737 A1 3/2014 Andreacchi et al.
2014/0076739 A1 3/2014 Andreacchi
2014/0155979 A1 6/2014 Lam et al.
2014/0271319 A1 9/2014 Zheng et al.
2014/0277392 A1 9/2014 Webler, Jr.
2014/0360887 A1 12/2014 Andreacchi et al.
2016/0002816 A1 1/2016 Andreacchi
2017/0296365 A1 10/2017 Kramer-Brown et al.
2018/0340245 A1 11/2018 Kernion et al.
2021/0106729 A1 4/2021 Simpson et al.

FOREIGN PATENT DOCUMENTS

CN 102356185 A 2/2012
CN 102481662 A 5/2012
CN 102552991 A 7/2012
CN 202412010 U 9/2012
CN 103252496 A 8/2013
CN 110306099 A 10/2019
EP 0804934 A2 11/1997
EP 1604691 A2 12/2005
EP 1632584 A1 3/2006
EP 1674118 A2 6/2006
EP 1731241 A1 12/2006
EP 1829982 A1 9/2007
EP 2054101 A2 5/2009
EP 2640432 A0 5/2012
EP 2676684 A1 12/2013
EP 2676686 A1 12/2013
EP 3138587 A1 8/2017
JP 07-090694 A 4/1995
JP 08-302500 A 11/1996
JP 09-508538 9/1997
JP 10-025531 A 1/1998
JP 2001-001124 A 1/2001
JP 2002-503529 2/2002
JP 2002-069555 A 3/2002
JP 2003-267609 A 9/2003
JP 2006-519068 8/2006
JP 2008-188670 A 8/2008
WO 97/33534 A1 9/1997
WO 99/15108 A2 4/1999
WO 00/54704 A1 9/2000
WO 00/69368 A2 11/2000
WO 01/15632 A1 3/2001
WO 01/17577 A1 3/2001
WO 01/61080 A1 8/2001
WO 01/72349 A1 10/2001
WO 02/78763 10/2002
WO 2007/103446 A2 9/2007
WO 2008/022126 A1 2/2008
WO 2009/126431 A2 10/2009
WO 2010/081723 A1 7/2010
WO 2010/107798 A1 9/2010
WO 2012/068358 A1 5/2012
WO 2013/162690 A1 10/2013
WO 2014/159743 A1 10/2014
WO 2014/159747 A1 10/2014
WO WO-2019164062 A1 * 8/2019 ................ C22F 1/10

OTHER PUBLICATIONS

English Abstract and English Machine Translation of Choi (WO 2019/164062 A1) (Aug. 29, 2019).*

(56) References Cited

OTHER PUBLICATIONS

U.S. Appl. filed Nov. 17, 2010, Boylan., U.S. Appl. No. 61/414,566.
U.S. Appl. No. 11/370,642, filed Apr. 12, 2010, Notice of Allowance.
U.S. Appl. No. 11/370,642, filed Sep. 22, 2009, Office Action.
U.S. Appl. No. 11/736,979, filed Apr. 10, 2013, Issue Notification.
U.S. Appl. No. 13/271,869, filed Apr. 1, 2013, Office Action.
U.S. Appl. No. 13/271,869, filed Apr. 26, 2013, Office Action.
U.S. Appl. No. 13/271,869, filed Jul. 9, 2014, Issue Notification.
U.S. Appl. No. 13/271,869, filed Mar. 18, 2014, Notice of Allowance.
U.S. Appl. No. 13/271,869, filed Nov. 27, 2013, Office Action.
U.S. Appl. No. 13/617,877, filed Apr. 18, 2014, Office Action.
U.S. Appl. No. 13/617,877, filed Dec. 20, 2013, Office Action.
U.S. Appl. No. 13/617,877, filed Sep. 14, 2012, Anthony S. Andreacchi, Sep. 23, 2014, Office Action.
U.S. Appl. No. 13/617,877, filed Sep. 23, 2014, Office Action.
U.S. Appl. No. 13/618,348, filed Apr. 16, 2014, Notice of Allowance.
U.S. Appl. No. 13/618,348, filed Dec. 19, 2013, Office Action.
U.S. Appl. No. 13/618,348, filed Sep. 14, 2012, Anthony S. Andreacchi, Apr. 16, 2014, Notice of Allowance.
U.S. Appl. No. 13/618,348, filed Sep. 14, 2012, Anthony S. Andreacchi, Aug. 6, 2014, Issue Notification.
U.S. Appl. No. 13/618,407, Dec, 2, 2014, Office Action.
U.S. Appl. No. 13/618,407, Mail Date May 13, 2015, Notice of Allowance.
U.S. Appl. No. 13/618,455, filed Feb. 2, 2015, Notice of Allowance.
U.S. Appl. No. 13/618,455, filed Sep. 14, 2012, Andreacchi et al.
U.S. Appl. No. 13/618,455, Mail Date May 13, 2015, Issue Notification.
U.S. Appl. No. 13/618,455, Mail Date May 8, 2014, Office Action.
U.S. Appl. No. 13/618,455, Mail Date Sep. 25, 2014, Office Action.
U.S. Appl. No. 13/618,455, filed May 8, 2014, Office Action.
U.S. Appl. No. 13/618,455, filed Sep. 25, 2014, Office Action.
U.S. Patent Application filed on Mar. 14, 2013, by Kramer-Brown et al., U.S. Appl. No. 13/830,404.
U.S. Appl. No. 11/736,979, filed Feb. 20, 2013, Issue Notification.
Wang et al. Microstructure and mechanical properties of CoCrFeNiWx high entropy alloys reinforced by u phase particles. Journal of Alloys and Compounds 843 (2020) 155997. (Year: 2020).
Zhang et al. Phase transformations in Co—Ni—Cr—W alloys during high temperature exposure to steam environment. J. Phase Equil. Diffus. (2018) 39:387-400. (Year: 2018).
Advisory Action received for U.S. Appl. No. 15/670,761, mailed on Jan. 12, 2022, 3 pages.
Advisory Action received for U.S. Appl. No. 15/670,761, mailed on Mar. 16, 2021, 3 pages.
Campbell, ed. Chapter 16 Nonequilbrium Reactions—Precipitation Hardening. Phase Diagrams Understanding the Basics. ASM International. 2012. 339-361. (Year: 2012).
CN 101554685 machine translation (Year: 2009).
CN 103252496 machine translation (Year: 2013).
CN 110306099 machine translation (Year: 2019).
Cordis Palmaz Blue .018 Peripheral Stent System, Johson & Johnson Medical NV/SA, May 2005 (2 pages) http://www.jjnordic.com/Lists/FileList1/Attatchments/174/PalmazBlue.sub.—-018.sub.—Brochure.PDF.
Dinega, Dmitry P., and M. G. Bawendi. "A solution-phase chemical approach to a new crystal structure of cobalt." Angewandte Chemie International Edition 38.12 (1999): 1788-1791.
Donachie et al. Chapter 7 Powder Metallurgy Processing. Superalloys A Technical Guide. Second Edition. 2002. ASM International. 117-134. (Year: 2002).
Duerig, T. W., Melton, K. N., & Stockel, D. (2013), Engineering aspects of shape memory alloys. Butterworth-Heinemann, 414-419.
Eutectic system. In Wikipedia, The Free Encyclopedia. Retrieved 11:54, Apr. 27, 2010, 1-5, from https://en.wikipedia.org/w/index.php?title=Eutectic_system&oldid=702728275.
Final Office Action received for U.S. Appl. No. 15/670,761, mailed on Jan. 27, 2021, 13 pages.
Final Office Action received for U.S. Appl. No. 15/670,761, mailed on Oct. 29, 2021, 15 pages.
Final Office Action received for U.S. Appl. No. 16/601,259, mailed on Sep. 23, 2021, 11 pages.
Forging of Niobium, tantalum, and their alloys, MetalPass, accessed Apr. 18, 2013. http://www.metalpass.com/metaldoc/paper.aspx?docID=312.
Giessen et al., "Coronary Stenting with a New Radiopaque Balloon Expandable Endoprosthesis in Pigs", Circulation, vol. 83, No. 5, May 1991, pp. 1788-1798.
Gold. In Wikipedia, The Free Encyclopedia. Revised on Apr. 22, 2010, Retrieved 11:11, Aug. 7, 2017, 1-21, from https://en.wikipedia.org/w/index.php?title=Gold&diff=357659233&oldid=357425502.
Indium. (Feb. 25, 2016). In Wikipedia, The Free Encyclopedia. Retrieved 12:13, Apr. 27, 2010, 1-7, from https://en.wikipedia.org/w/index.php?title=Indium&oldid=706790732.
International Search Report and Written Opinion of the International Searching Authority dated Sep. 26, 2007, for related PCT Application No. PCT/US2007/05844.
Issue Notification received for U.S. Appl. No. 09/534,071, mailed on Jul. 11, 2007.
Issue Notification received for U.S. Appl. No. 13/172,278 mailed on Jul. 19, 2017.
Issue Notification received for U.S. Appl. No. 13/548,908 mailed on Mar. 11, 2015.
Issue Notification received for U.S. Appl. No. 13/618,348 mailed on Aug. 6, 2014.
Issue Notification received for U.S. Appl. No. 13/618,602, mailed on Sep. 17, 2014.
Jacobson, D. M., & Humpston, G, (1989). Gold coatings for fluxless soldering. Gold Bulletin, 22(1), 9-18.
Liu. 2 Processes and Techniques for Droplet Generation. Science and Engineering of Droplets. Notes Publications. 2000. 19-120. (Year: 2000).
Narushima, Precipitates-in-Biomedical-Co-Cr-Alloys_Narushima-Mineta-Kurihara-Ueda_Publishedonline-Feb. 26, 2013, Feb. 26, 2013, JOM, vol. 65, No. 4, 2013, 489, 65.
Non-Final Office Action received for U.S. Appl. No. 15/670,761, mailed on Jul. 20, 2021, 14 pages.
Non-Final Office Action received for U.S. Appl. No. 15/670,761, mailed on Jun. 1, 2022, 11 pages.
Non-Final Office Action received for U.S. Appl. No. 15/670,761, mailed on Oct. 15, 2020, 14 pages.
Non-Final Office Action received for U.S. Appl. No. 16/601,259, mailed on May 17, 2021, 11 pages.
Non-Final Office Action received for U.S. Appl. No. 17/068,526, mailed on Oct. 5, 2022, 35 pages.
Notice of Allowance received for U.S. Appl. No. 09/534,071, mailed on Feb. 12, 2007.
Notice of Allowance received for U.S. Appl. No. 11/736,979, mailed on Nov. 9, 2012.
Notice of Allowance received for U.S. Appl. No. 12/100,991 mailed on Aug. 17, 2012.
Notice of Allowance received for U.S. Appl. No. 13/172,278 mailed on Apr. 11, 2017.
Notice of Allowance received for U.S. Appl. No. 13/548,908 mailed on Dec. 2, 2014.
Notice of Allowance received for U.S. Appl. No. 13/617,877, mailed on May 28, 2015.
Notice of Allowance received for U.S. Appl. No. 13/618,348 mailed on Aug. 6, 2014.
Notice of Allowance received for U.S. Appl. No. 13/618,407, mailed on May 13, 2015.
Notice of Allowance received for U.S. Appl. No. 13/618,455 mailed on Feburary 02, 2015.
Notice of Allowance received for U.S. Appl. No. 13/618,455, mailed on Febraury 02, 2015.
Notice of Allowance received for U.S. Appl. No. 14/466,513 mailed on Mar. 28, 2017.
Notice of Allowance received for U.S. Appl. No. 16/601,259, mailed on Dec. 6, 2021, 8 pages.
Notice of Allowance received for U.S. Appl. No. 16/601,259, mailed on Mar. 9, 2022, 6 pages.

(56) References Cited

OTHER PUBLICATIONS

Notice of Allowance received for U.S. Appl. No. 11/370,642 mailed on Apr. 12, 2010.
Notice of Allowance received for U.S. Appl. No. 13/618,602, mailed on May 27, 2014.
Notice of Allowance received for U.S. Appl. No. 13/830,404, mailed on Oct. 18, 2016.
Notice of Allowance received for U.S. Appl. No. 15/429,339, mailed on Jun. 5, 2019.
Notification of Transmittal of the International Search Report and the Written Opinion of the International Searching Authority, or the Declaration, Patent Cooperation Treaty, European Patent Office, Dec. 29, 2009 (12 pages).
Office Action received for U.S. Appl. No. 09/534,071, mailed on Aug. 29, 2005.
Office Action received for U.S. Appl. No. 09/534,071, mailed on Dec. 18, 2002.
Office Action received for U.S. Appl. No. 09/534,071, mailed on Mar. 13, 2006.
Office Action received for U.S. Appl. No. 09/534,071, mailed on Nov. 15, 2005.
Office Action received for U.S. Appl. No. 09/534,071, mailed on Sep. 13, 2006.
Office Action received for U.S. Appl. No. 09/534,071, mailed on Sep. 17, 2002.
Office Action received for U.S. Appl. No. 11/370,642 mailed on Sep. 22, 2009.
Office Action received for U.S. Appl. No. 11/736,979, mailed on Apr. 4, 2011.
Office Action received for U.S. Appl. No. 11/736,979, mailed on Apr. 12, 2012.
Office Action received for U.S. Appl. No. 11/736,979, mailed on Aug. 31, 2010.
Office Action received for U.S. Appl. No. 11/736,979, mailed on May 26, 2010.
Office Action received for U.S. Appl. No. 11/736,979, mailed on Sep. 19, 2011.
Office Action received for U.S. Appl. No. 12/100,991 mailed on Dec. 21, 2011.
Office Action received for U.S. Appl. No. 12/100,991 mailed on Sep. 29, 2011.
Office Action received for U.S. Appl. No. 13/172,278 mailed on Apr. 3, 2015.
Office Action received for U.S. Appl. No. 13/172,278 mailed on Jun. 10, 2013.
Office Action received for U.S. Appl. No. 13/172,278 mailed on Nov. 21, 2013.
Office Action received for U.S. Appl. No. 13/172,278 mailed on Oct. 8, 2015.
Office Action received for U.S. Appl. No. 13/172,278 mailed on Sep. 19, 2016.
Office Action received for U.S. Appl. No. 13/271,869 mailed on Apr. 26, 2013.
Office Action received for U.S. Appl. No. 13/271,869 mailed on Nov. 27, 2013.
Office Action received for U.S. Appl. No. 13/548,908 mailed on Jun. 18, 2014.
Office Action received for U.S. Appl. No. 13/617,877 mailed on Apr. 18, 2014.
Office Action received for U.S. Appl. No. 13/617,877 mailed on Dec. 20, 2013.
Office Action received for U.S. Appl. No. 13/617,877 mailed on Sep. 23, 2014.
Office Action received for U.S. Appl. No. 13/618,348 mailed on Dec. 19, 2013.
Office Action received for U.S. Appl. No. 13/618,407, mailed on Dec. 2, 2014.
Office Action received for U.S. Appl. No. 13/618,455 mailed on May 8, 2014.
Office Action received for U.S. Appl. No. 13/618,455 mailed on Sep. 25, 2014.
Office Action received for U.S. Appl. No. 13/618,602, mailed on May 3, 2013.
Office Action received for U.S. Appl. No. 09/534,071, mailed on Jul. 9, 2003.
Office Action received for U.S. Appl. No. 13/298,070, mailed on Jun. 25, 2014.
Office Action received for U.S. Appl. No. 13/298,070, mailed on Oct. 6, 2014.
Office Action received for U.S. Appl. No. 13/618,602, mailed on Aug. 20, 2013.
Office Action received for U.S. Appl. No. 13/618,602, mailed on Jan. 6, 2014.
Office Action received for U.S. Appl. No. 13/830,404, mailed on Apr. 20, 2016.
Office Action received for U.S. Appl. No. 13/830,404, mailed on Aug. 10, 2016.
Office Action received for U.S. Appl. No. 13/830,404, mailed on Jan. 8, 2016.
Office Action received for U.S. Appl. No. 13/830,404, mailed on May 29, 2015.
Office Action received for U.S. Appl. No. 13/830,404, mailed on Sep. 16, 2015.
Office Action received for U.S. Appl. No. 15/429,339, mailed on Feb. 26, 2019.
Ohring et al. "A Versatile Arc Melting Apparatus for Quenching Molten Metals and Ceramics." Review of Scientific instruments 42.4 (1971): 530-531.
Poletti et al. Development of a new high entropy alloy for wear resistance: FeCoCrNiW0.3 and FeCoCrNiW0.3+5 at% of C. Materials and Design 115 (2017) 247-254. (Year: 2017).
Restriction Requirement received for U.S. Appl. No. 13/618,602, mailed on Mar. 4, 2013.
Restriction Requirement received for U.S. Appl. No. 17/068,526, mailed on Jul. 15, 2022, 6 pages.
Restriction Requirement received for U.S. Appl. No. 13/298,070, mailed on May 2, 2014.
Shang. CoCrFeNi(W1-xMox) high-entropy alloy coatings with excellent mechanical properties and corrosion resistance prepared by mechanical alloying and hot pressing sintering. Materials and Design 117 (2017) 193-202. (Year: 2017).
Sheng. A Co—Cr—Ni—W—C alloy processed by multiple rolling. Strength of Materials, vol. 52, No. 1, Jan. 2020. (Year: 2020).
Tanaka. Effects of high-temperature ageing on the creep-rupture properties of high-tungsten cobalt-base superalloys. Journal of Materials Science 29 (1994) 2620-2628. (Year: 1994).
Tin. In Wikipedia, The Free Encyclopedia. Retrieved 12:08, Apr. 27, 2010, 1-15, from https://en.wikipedia.org/w/index.php?title=Tin&oldid=708568728.
Advisory Action (PTOL-303) Mailed on Apr. 15, 2020 for U.S. Appl. No. 15/670,761, 3 page(s).
Advisory Action (PTOL-303) Mailed on Feb. 14, 2014 for U.S. Appl. No. 13/172,278, 3 page(s).
Final Rejection Mailed on Feb. 24, 2023 for U.S. Appl. No. 17/068,526, 24 page(s).
Final Rejection Mailed on Jan. 11, 2023 for U.S. Appl. No. 17/562,592, 7 page(s).
Final Rejection Mailed on Mar. 3, 2020 for U.S. Appl. No. 15/670,761, 11 page(s).
Final Rejection Mailed on Oct. 28, 2024 for U.S. Appl. No. 18/321,265, 15 page(s).
Final Rejection Mailed on Sep. 15, 2022 for U.S. Appl. No. 15/670,761, 14 page(s).
Non-Final Rejection Mailed on Jan. 19, 2024 for U.S. Appl. No. 17/068,526, 32 page(s).
Non-Final Rejection Mailed on Jul. 11, 2024 for U.S. Appl. No. 18/321,265, 13 page(s).
Non-Final Rejection Mailed on Jun. 18, 2025 for U.S. Appl. No. 18/321,265, 17 page(s).
Non-Final Rejection Mailed on Mar. 22, 2024 for U.S. Appl. No. 18/217,833, 14 page(s).

(56) References Cited

OTHER PUBLICATIONS

Non-Final Rejection Mailed on Oct. 30, 2019 for U.S. Appl. No. 15/670,761, 14 page(s).
Non-Final Rejection Mailed on Sep. 30, 2022 for U.S. Appl. No. 17/562,592, 8 page(s).
Non-Final Rejection Mailed on Sep. 30, 2025 for U.S. Appl. No. 18/321,265, 18 page(s).
Notice of Allowance and Fees Due (PTOL-85) Mailed on Apr. 5, 2023 for U.S. Appl. No. 17/562,592, 7 page (s).
Notice of Allowance and Fees Due (PTOL-85) Mailed on Apr. 20, 2023 for U.S. Appl. No. 15/670,761, 7 page (s).
Notice of Allowance and Fees Due (PTOL-85) Mailed on Apr. 27, 2023 for U.S. Appl. No. 17/562,592, 2 page (s).
Notice of Allowance and Fees Due (PTOL-85) Mailed on Aug. 23, 2013 for U.S. Appl. No. 13/271,501, 12 page (s).
Notice of Allowance and Fees Due (PTOL-85) Mailed on Aug. 23, 2013 for U.S. Appl. No. 13/271,860, 12 page (s).
Notice of Allowance and Fees Due (PTOL-85) Mailed on Aug. 29, 2013 for U.S. Appl. No. 13/271,504, 11 page (s).
Notice of Allowance and Fees Due (PTOL-85) Mailed on Jul. 17, 2023 for U.S. Appl. No. 15/670,761, 6 page (s).
Notice of Allowance and Fees Due (PTOL-85) Mailed on Jul. 17, 2024 for U.S. Appl. No. 18/217,833, 9 page (s).
Notice of Allowance and Fees Due (PTOL-85) Mailed on Jul. 19, 2024 for U.S. Appl. No. 17/068,526, 11 page (s).
Notice of Allowance and Fees Due (PTOL-85) Mailed on Jun. 19, 2015 for U.S. Appl. No. 13/617,877, 4 page (s).
Notice of Allowance and Fees Due (PTOL-85) Mailed on May 15, 2023 for U.S. Appl. No. 17/562,592, 7 page (s).
Office Action received for U.S. Appl. No. 13/615,540, mailed on Aug. 23, 2013.
Office Action received for U.S. Appl. No. 13/615,540, mailed on Dec. 31, 2012.
Office Action received for U.S. Appl. No. 13/615,540, mailed on Feb. 7, 2014.
Office Action received for U.S. Appl. No. 13/615,540, mailed on Jun. 19, 2013.
Office Action received for U.S. Appl. No. 13/830,096, mailed on Dec. 1, 2015.
Office Action received for U.S. Appl. No. 14/667,279, mailed on Jul. 28, 2016.
Office Action received for U.S. Appl. No. 14/852,263, mailed on May 18, 2017.
Requirement for Restriction/Election Mailed on Aug. 15, 2019 for U.S. Appl. No. 15/670,761, 7 page(s).

* cited by examiner

PROCESSING OF COBALT-TUNGSTEN ALLOYS

CROSS-REFERENCE TO RELATED APPLICATIONS

This application claims the benefit of and priority to U.S. Provisional Patent Application No. 63/350,106 (WN 17066.146) filed Jun. 8, 2022, which is herein incorporated by reference in its entirety.

BACKGROUND

Intraluminal stents implanted with percutaneous methods have become a standard adjunct to procedures such as balloon angioplasty in the treatment of atherosclerotic disease of the arterial system. Stents, by preventing acute vessel recoil, improve long-term patient outcome and have other benefits such as securing vessel dissections.

Intraluminal stents comprise generally tubular-shaped devices that are constructed to hold open a segment of a blood vessel or other anatomical lumen. Intraluminal stents are used in treatment of diseases such as atherosclerotic stenosis as well as diseases of the stomach and esophagus, and for urinary tract applications. Adequate stent function requires a precise placement of the stent over a lesion or site of plaque or other lumen site in need of treatment. Typically, the stent is delivered to a treatment site by a delivery catheter that comprises an expandable portion for expanding the stent within the lumen.

The delivery catheter onto which the stent is mounted may be a balloon delivery catheter similar to those used for balloon angioplasty procedures. In order for the stent to remain in place on the balloon during delivery to the site of damage within a lumen, the stent may be compressed onto the balloon. The catheter and stent assembly is introduced within a patient's vasculature using a guide wire. The guide wire is disposed across the damaged arterial section and then the catheter-stent assembly is advanced over the guide wire within the artery until the stent is directly within the lesion or the damaged section.

The balloon of the catheter is expanded, expanding the stent against the artery wall. The artery is preferably slightly expanded by the expansion of the stent to seat or otherwise fix the stent to prevent movement. In some circumstances during treatment of stenotic portions of the artery, the artery may have to be expanded considerably in order to facilitate passage of blood or other fluid therethrough. In the case of a self-expanding stent, the stent is expanded by retraction of a sheath or actuation of a release mechanism. Self-expanding stents may expand to the vessel wall automatically without the aid of a dilation balloon, although such a dilation balloon may be used for another purpose.

These manipulations are performed within the body of a patient by a practitioner who may rely upon both placement markers on the stent catheter and on the radiopacity of the stent itself. The stent radiopacity arises from a combination of stent material and stent pattern, including stent strut or wall thickness. After deployment within the vessel, the stent radiopacity should allow adequate visibility of both the stent and the underlying vessel and/or lesion morphology under fluoroscopic visualization.

Stent radiopacity relies on the use of materials having high density, a high atomic number and/or a high electron density contrast compared to the stent's surroundings. Although a variety of alloy materials are available, there remains a need for improved alloy materials, exhibiting enhanced properties, as well as methods for processing such alloys, e.g., to ensure they exhibit fine grain structure and/or minimal inclusions.

SUMMARY

In particular, many proposed alloys do not provide the desired substantially homogenous, single-phase structure once manufactured, but instead include the presence of a multiphase microstructure with precipitates or inclusions of a second phase of significant particle size, which can lead to problems during processing steps such as drawing, cutting and electropolishing. For example, the occurrence of relatively large precipitates or inclusions of a second phase can lead to selective attack of one phase at the expense of another, crack propagation at the boundaries of such precipitates or inclusions, and the like, making it difficult or impossible as a practical matter to provide desired mechanical performance properties in the resulting stent.

A need therefore continues to exist for stent alloys that achieve enhanced radiopacity, particularly where the alloy includes a significant fraction of a platinum group metal, refractory metal, or other precious or exotic metal as radiopacifiers, while minimizing or eliminating the occurrence of inclusions of a secondary phase throughout manufacturing, processing, and use. The present disclosure thus relates to processing methods that can be used to substantially eliminate the occurrence of such a secondary phase from a cobalt-chromium alloy that includes platinum or another radiopacifying metal, as described herein. While alloys including cobalt and chromium with platinum as a particularly contemplated radiopacifier benefit from the present processing methods, it will be appreciated that the present methods may also be applicable to other alloys, e.g., using additional or other high density, high atomic number radiopacifier metals, such as the various platinum group metals, precious metals, or refractory metals and the alloys thereof described in applicant's U.S. Pat. Nos. 9,566,147; 10,441,445, and application Ser. Nos. 16/601,259; 17/068,526 and 17/562,592, each of which is herein incorporated by reference in its entirety. The presently described methods have been found to surprisingly result in dissolution of secondary phase precipitates (e.g., tungsten rich precipitates) present in such alloys, even where similar treatments at higher temperature and/or longer treatment times were ineffective in achieving dissolution of such precipitates.

One embodiment of the present disclosure includes a process for producing a substantially homogenous cobalt-chromium alloy including tungsten and at least one of a platinum group metal, a precious metal, refractory metal, or other radiopacifying element having an atomic number and/or density greater than that of cobalt. Such a process may include providing an alloy formed from cobalt, chromium, tungsten, and at least one of a platinum group metal, precious metal, refractory metal, or other radiopacifying element having an atomic number and/or density greater than that of cobalt and heating the alloy to a temperature of about 1250° C. for a time period of about 30 minutes, and rapidly quenching the alloy to 600° C. or less within about 5 minutes (e.g., within 1 minute or less). As noted, longer treatment times (e.g., 60 minutes at 1250° C.) and/or higher temperatures (e.g., 1275° C. for 60 minutes) were actually ineffective in resolving the presence of secondary phase precipitates.

Another exemplary process for producing a substantially homogenous cobalt-chromium alloy including cobalt, chromium, tungsten and platinum may include providing the alloy formed from cobalt, chromium, tungsten and platinum, wherein said alloy includes precipitate inclusions, so as to not be substantially homogenous. The alloy having such precipitate inclusions is heated to a temperature from about 1225° C. to 1275° C. for a time period from about 20 minutes to 40 minutes to substantially remove the precipitate inclusions from the alloy, providing a substantially homogenous alloy, followed by rapidly quenching the alloy to 600° C. or less within about 5 minutes (e.g., within 1 minute or less).

Another exemplary process for producing a stent formed from a substantially homogenous cobalt chromium alloy including cobalt, chromium, tungsten and platinum may include providing the alloy in the form of a tube or rod formed from cobalt, chromium, tungsten, and platinum, where said alloy includes precipitate inclusions so as to not be substantially homogenous, and heating the alloy to a temperature from about 1225° C. to 1275° C. for a time period from about 20 to 40 minutes to remove the precipitate inclusions from the alloy, providing a substantially homogenous alloy. After such heating, the alloy is rapidly quenched to 600° C. or less within about 5 minutes (e.g., within 1 minute or less), and the tube or rod is drawn to form the desired stent.

In an embodiment, the alloy comprises cobalt, chromium, tungsten, and platinum. In an embodiment, the alloy may not include any other elements in amounts greater than about 10% by weight. For example, the alloy may include nickel in an amount of about 10% by weight, with no other elements present in higher amounts. In an embodiment, any additional elements may be present in amounts no greater than 5%, no greater than 3%, no greater than 2%, or no greater than 1% by weight.

In an embodiment, rapid quenching may be performed within a time period of less than 5 minutes, less than 3 minutes, less than 2 minutes, or less than 1 minute.

In an embodiment, the rapid quenching may be performed with water (e.g., by immersing the alloy in water).

In an embodiment, the alloy may include cobalt in an amount from about 20% to 40% by weight.

In an embodiment, the alloy may include chromium in an amount of about 20% by weight.

In an embodiment, the alloy may include nickel in an amount of about 10% by weight.

In an embodiment, the alloy may be substantially or entirely free of molybdenum (and/or other elements of the periodic table not mentioned herein).

In an embodiment, the alloy may be substantially or entirely free of carbon.

In an embodiment, the alloy may include no more than 1%, no more than no more than 0.1%, or no more than 0.05% by weight of one or more of silicon, phosphorus, or sulfur.

In an embodiment, the alloy may further include manganese in an amount of up to 5%, up to 3%, or up to 2% (e.g., 1-2%) by weight.

In an embodiment, the alloy may further include iron in an amount of up to 5%, up to 3%, or up to 2% (e.g., 0-3%) by weight.

In an embodiment, the alloy may further include both manganese and iron in an amount of up to about 3% each, by weight.

In an embodiment, the sum of the percentage of cobalt and platinum in the alloy may be from 48% to about 60%, or 50% to 57% (e.g., about 55%).

In an embodiment, the alloy may include:

about 20-37% cobalt;
about 20-30% platinum;
about 19-21% chromium;
about 14-16% tungsten;
about 9-11% nickel; and
about 1-2% manganese.

In an embodiment, the alloy may include one or more trace elements as follows:

iron;
sulfur;
phosphorus; and
silicon.

In an embodiment, the precipitate inclusions may include tungsten (e.g., $Co_3W$).

The alloy may be used to form a radiopaque stent. The radiopaque stent comprises a cylindrical main body, where the body is formed (e.g., entirely) from the substantially homogenous alloy as described herein.

The alloy may include chromium (e.g., in a concentration of about 20% by weight), and nickel in a concentration of 5-15% by weight (e.g., about 10% by weight), as well as small quantities of manganese (e.g., in a concentration of 0-5% by weight), iron (e.g., in a concentration of 0-5% by weight), as well as other trace elements as noted, e.g., in a concentration of 1% maximum, 0.5% maximum, 0.3% maximum, 0.2% maximum, 0.1% maximum, 0.05% maximum, or 0.01% maximum. Exemplary trace elements may include silicon (e.g., up to about 0.04%), phosphorus (up to about and sulfur (up to about 0.03%). Other trace elements typically present in an L-605 alloy (e.g., beryllium, boron, carbon) may be absent, or at least present at lower concentration than the L-605 standard permits.

The phrase "substantially free" as used herein may mean that if present, such a constituent is present in the alloy in an amount of less than 0.05%, less than 0.04%, less than 0.03%, less than 0.02%, less than 0.01%, less than 0.001%, or preferably 0% by weight.

The phrase "substantially homogenous" as used herein may mean that if any secondary phase precipitate phase is present, such is present in an amount of less than 2%, less than 1%, less than 0.5%, or less than 0.1% volume fraction of a secondary precipitate inclusion phase.

The particles of such a secondary precipitate inclusion phase may have a maximum or even average particle size of less than 5 μm, less than 4 μm, less than 3 μm, less than 2 μm, or less than 1 μm. As shown in the SEM images included herewith, any such secondary precipitate inclusion phase is finely dispersed, e.g., with a maximum or average particle size that may be less than 10%, less than 5%, less than 3%, less than 2%, or less than 1% of the wall thickness of a stent wall (e.g., about 100 μm). For example, where wall thickness may be from 50 to 100 μm, or from 75 to 100 μm, maximum or even average particle size of any finely dispersed secondary precipitate inclusion phase may be less than 10%, less than 5%, less than 3%, less than 2%, or less than 1% that of the wall thickness (e.g., 5 μm or less, 4 μm or less, 3 μm or less, 2 μm or less, or even 1 μm or less) so that the presence of any such precipitate inclusion has a minimal impact on desired mechanical properties. As noted herein, the presence of such precipitate inclusions can be substantially eliminated by heating the solid alloy to about 1250° C., for about 30 minutes followed by rapid quenching.

Features from any of the disclosed embodiments may be used in combination with one another, without limitation. For example, any of the compositional limitations described with respect to one embodiment may be present in any of the other described embodiments. In addition, other features and advantages of the present disclosure will become apparent to those of ordinary skill in the art through consideration of the following detailed description and the accompanying drawings.

BRIEF DESCRIPTION OF THE DRAWINGS

To further clarify the above and other advantages and features of the present disclosure, a more particular description will be rendered by references to specific embodiments thereof, which are illustrated in the appended drawings. It is appreciated that these drawings depict only typical embodiments of the invention and are therefore not to be considered limiting of its scope. The present disclosure will be described and explained with additional specificity and detail through the use of the accompanying drawings.

Figure 12A:
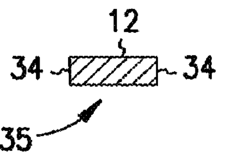
FIG. 12 is a plan view of a flattened section of a radiopaque stent configuration which can be formed according to the present invention, which illustrates an undulating pattern of the stent shown in FIG. 11.
Figure 12:
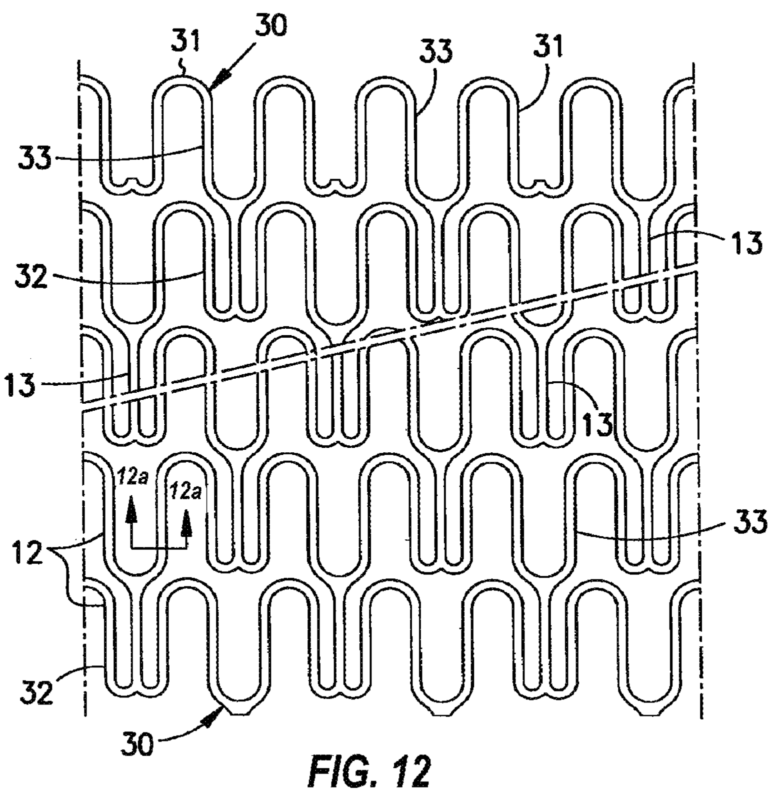

FIG. **12*a* is a sectional view taken along the line 12*a*-12*a* in FIG. 12**.

Figure 13:
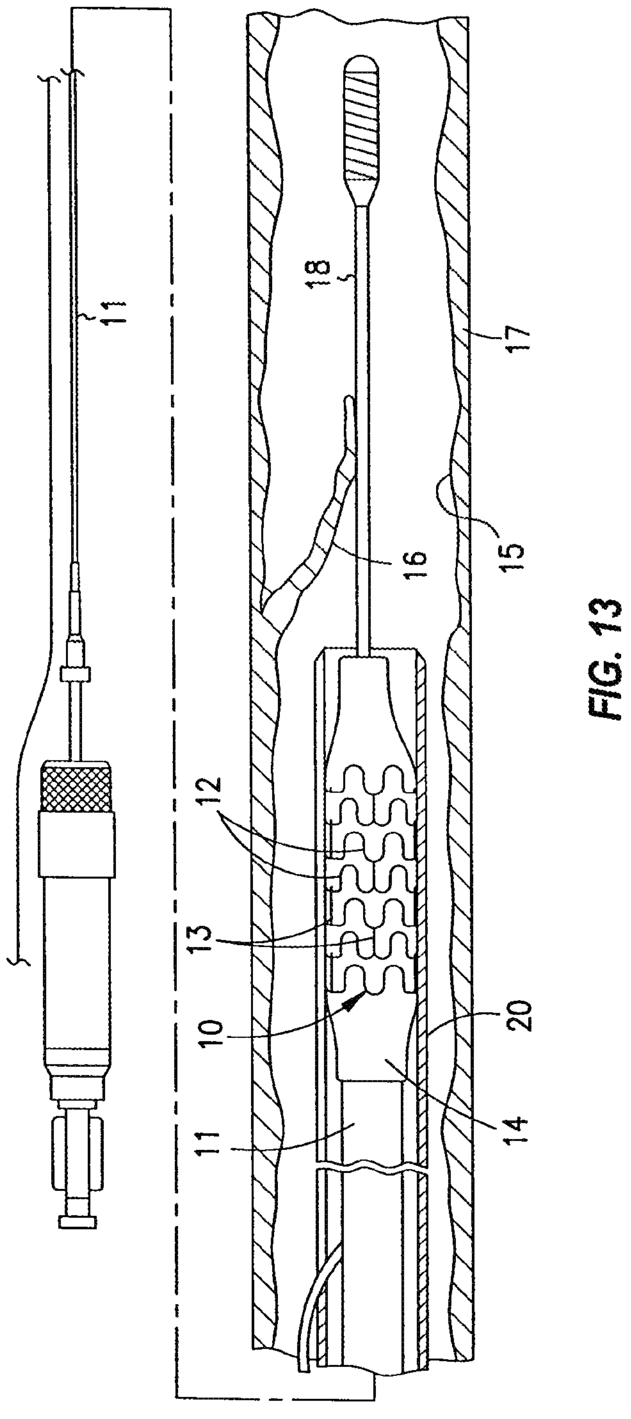

FIG. 13 is an elevational view, partially in section, of a radiopaque stent that can be formed according to the present invention, mounted on a delivery catheter and disposed within a damaged lumen.

Figure 14:
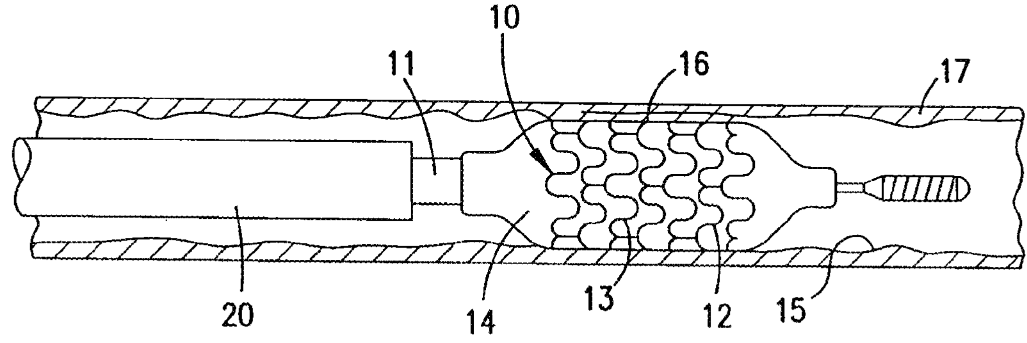

FIG. 14 is an elevational view, partially in section, showing the radiopaque stent of FIG. 13 within a damaged lumen.

Figure 15:
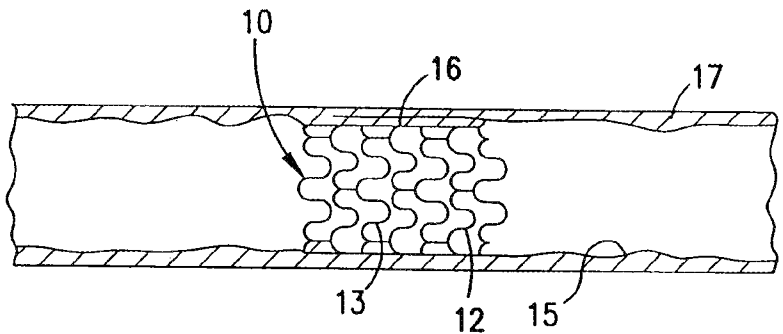

FIG. 15 is an elevational view, partially in section, showing the radiopaque stent of FIG. 13 expanded within the lumen after withdrawal of the delivery catheter.

Figure 16:
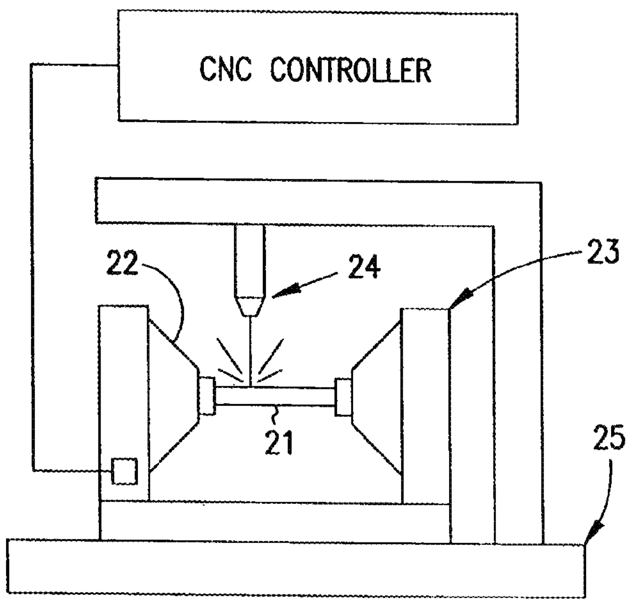

FIG. 16 is a schematic representation of equipment for selectively cutting the tubing in the manufacture of the radiopaque stent of the present invention.

DETAILED DESCRIPTION

I. Introduction

Many alloys proposed for use in construction of stents or similar implantable medical devices do not provide a substantially homogenous, single-phase structure once manufactured into the desired stent or other structure. Rather, such alloys may often include a multiphase microstructure with precipitates or inclusions of a secondary phase of significant particle size, which can lead to problems during processing steps such as drawing, cutting, and electropolishing, or potential problems during use. For example, the occurrence of relatively large precipitates or inclusions of a secondary phase can lead to selective attack of one phase at the expense of another, crack propagation at the boundaries of such precipitates or inclusions, and the like, making it difficult or impossible as a practical matter to provide desired mechanical performance in the resulting stent.

An embodiment of the present disclosure includes processes for processing alloys that include a significant fraction of a platinum group metal, refractory metal, or other precious or exotic metal having an atomic number and/or density greater than that of cobalt, as a radiopacifier, while minimizing or eliminating the occurrence of inclusions of a secondary phase throughout manufacturing, processing, and use. For example, the present disclosure relates to processing methods that can be used to substantially eliminate the occurrence of such a secondary phase from a cobalt-chromium alloy that includes platinum or another such radiopacifying metal that significantly increases radiopacity. While alloys including cobalt and chromium with platinum as a particularly contemplated radiopacifier benefit from the present processing methods, it will be appreciated that the present methods may also be applicable to other alloys, e.g., using additional or other high density, high atomic number radiopacifier metals, such as the various platinum group metals, precious metals, or refractory metals and the alloys thereof described in applicant's U.S. Pat. Nos. 9,566,147; 10,441,445, and application Ser. Nos. 16/601,259; 17/068,526 and 17/562,592, each of which is herein incorporated by reference in its entirety. A wide variety of radiopacifier metals may be possible, including metals other than those described in the above referenced patents, so long as they are capable of forming a substantially homogenous single phase alloy, with increased radiopacity as compared to the cobalt being replaced.

An embodiment of the present disclosure includes a process for producing a substantially homogenous cobalt-chromium alloy including tungsten and at least one of a platinum group metal, a precious metal, refractory metal, or other selected metal as described herein to increase radiopacity. Such a process may include providing an alloy formed from cobalt, chromium, tungsten, and at least one of a platinum group metal, precious metal, refractory metal or other metal selected to increase radiopacity, and heating the alloy to a temperature of about 1250° C. for a time period of about 30 minutes, and rapidly quenching the alloy to 600° C. or less within about 5 minutes.

Another exemplary process for producing a substantially homogenous cobalt-chromium alloy including cobalt, chromium, tungsten and platinum may include providing the alloy formed from cobalt, chromium, tungsten and platinum, wherein said alloy can include precipitate inclusions, so as to not be substantially homogenous. The alloy that may have such precipitate inclusions is heated to a temperature from about 1225° C. to about 1275° C. (preferably less than 1300° C. to avoid incipient melting) for a time period from about 20 to 40 minutes to remove any precipitate inclusions from the alloy, providing a substantially homogenous alloy, and rapidly quenching the alloy to 600° C. or less within about 5 minutes.

Another exemplary process for producing a stent formed from a substantially homogenous cobalt chromium alloy including cobalt, chromium, tungsten and platinum may include providing the alloy in the form of a tube or rod formed from cobalt, chromium, tungsten, and platinum, where said alloy may include precipitate inclusions so as to not be substantially homogenous, and heating the alloy to a temperature from about 1225° C. to about 1275° C. for a time period from about 20 to 40 minutes to remove any precipitate inclusions from the alloy, providing a substantially homogenous alloy. After such heating, the alloy is rapidly quenched to 600° C. or less within about 5 minutes, and the tube or rod can be drawn to form the desired stent.

II. Exemplary Processes and Alloys

The radiopaque stent of the present disclosure comprises a main body, one embodiment of which is illustrated generally at 10 in FIG. 13, which can be fabricated from an alloy comprising cobalt-chromium-tungsten (Co—Cr—W), as well as an additional element providing radiopacity greater than that afforded by cobalt (e.g., addition of platinum). By way of example, the alloy may include at least 10%, at least 15%, or at least 20%, no more than 35%, or no more than 30%, such as from about 20% to about 30% by weight platinum. Nickel may also be present (e.g., in an amount of from 5-15%, such as about 10%). In particular, the alloy can be free or substantially free of precipitate inclusions present within the alloy structure. For example, the alloy can instead be in the form of a substantially single-phase microstructure, without (or substantially without) the presence of such precipitates or inclusions. This allows the alloy from which the stent is formed to be capable of deforming in a ductile manner, rendering the radiopaque stent of the present disclosure expandable. The substantial absence of such precipitates or inclusions also minimizes any tendency for microcracks or similar undesirable mechanical problems to occur.

The radiopaque Co—Cr—W alloy may be similar to L-605, but in which an amount of platinum is provided, e.g., reducing the amount of cobalt accordingly relative to L-605. Such an alloy may be referred to by applicant as P-605. The remaining weight fractions of other alloying elements in L-605 may remain unaltered (other than cobalt, which decreases). For example, alloy L-605 contains 14-16% by weight tungsten, 19-21% by weight chromium, 9-11% by weight nickel, 1-2% manganese, with a balance (other than trace elements) being cobalt. In the contemplated P-605 alloy, the cobalt may be present in an amount of from 20-40%, or 20-37%, where platinum is present at by weight. By including a substantial fraction of platinum (by substituting some of the cobalt), while retaining the remaining weight fractions, the relative radiopacity of the resulting P-605 alloy is increased relative to L-605, and where care is taken during manufacture and processing of the alloy as described herein, the resulting alloy can advantageously have a substantially homogenous single-phase microstructure with little to no presence of precipitates or inclusions. It will be appreciated that many other alloys that may nominally include such fractions of platinum, cobalt, chromium, tungsten and nickel will not necessarily include the required substantially homogenous single-phase structure without the presence of precipitates or inclusions, but will include coarse precipitate secondary phases present in the alloy, as shown in the accompanying SEM images (e.g., see particularly FIG. 1 and FIG. 4).

In particular, applicant has found that a substantially homogenous single-phase structure, with minimal if any precipitates or inclusions can be achieved by using a very specific heat treatment regimen, where the alloy that includes (or may include) such precipitates or inclusions is heated to a temperature of from 1225° C. to about 1275° C. (e.g., about 1250° C.) for a time period of from about 20 minutes to about 40 minutes to remove any precipitate inclusions that may be present within the alloy, followed by rapidly quenching the alloy to 600° C. or less within about 5 minutes (e.g., typically within 1 minute). Surprisingly, applicant has discovered that while the above noted process works to remove secondary phase precipitates that are present in such an alloy, superficially similar appearing treatments, at similar temperatures (e.g., 1225° C., 1250° C., 1275° C., or 1300° C.) for longer time periods such as 60 minutes, 2 hours, 12 hours, 24 hours, or 48 hours, are unsuccessful in removing such precipitates. It is surprising that the shorter heat treatment works, while a longer heat treatment does not, even at the same temperature.

Thus in an embodiment, the heat treatment is shorter than 60 minutes, such as no more than 50 minutes, or no more than about 40 minutes. In an embodiment, the heat treatment is at least 10 minutes, at least 15 minutes, or at least 20 minutes, such as about minutes. One particular combination of time and temperature that has been observed to work well is 30 minutes at 1250° C. Lower temperatures may be insufficient to dissolve precipitates that may be present, while slightly higher temperatures (e.g., greater than 1275° C., such as 1300° C.) may be so high as to result in undesirable incipient melting.

One embodiment of the radiopaque Co—Cr—Ni—W—Pt alloy of the present disclosure is comprised of chromium in a concentration of about 20% (e.g., 15% to 25%) by weight, tungsten in a concentration that is about 15% (e.g., at least 10%, such as 10-20% by weight, nickel in a concentration of 5-15% (e.g., about 10%) by weight, manganese in a concentration of 0-5% (e.g., 1-3%) by weight, and iron in a concentration of 0-5% (e.g., 0-3%, or 1-3%) by weight. Trace elements may be present, if at all, in concentrations of less than 1%, less than 0.5%, less than 0.4%, less than less than 0.2%, less than 0.1%, less than 0.05%, less than 0.04%, less than 0.03%, less than 0.02%, or less than 0.01% by weight. Platinum or another metal selected to provide greater radiopacity than cobalt may be present in an amount of about 25%, such as from 15% to 40%, or 20% to 35%, or 20% to 30% by weight. The balance of material may be cobalt, e.g., typically from about 20% to 40%, 20% to 35%, or 25% to 32% by weight. In an embodiment, the weight fractions for one or more of chromium, tungsten, manganese, iron, or nickel may be identical to those in L-605 (hence the applicant's reference to the alloy as P-605). In an embodiment, the fractions of cobalt and platinum may be the only significant difference in composition relative to L-605, although the sum of the cobalt+ platinum weight fractions may be equal to that of cobalt in L-605 (e.g., about 55%, such as 48-57%, or 50-57% by weight).

According to a further embodiment of the radiopaque Co—Cr—Ni—W—Pt alloy, the alloy may be substantially or entirely free of molybdenum and/or carbon as deliberately added alloying elements. "Substantially free" as used herein may include less than 2%, less than 1.5%, less than 1%, less than 0.5%, less than 0.15%, less than less than 0.05%, less than 0.04%, less than 0.03%, less than 0.02%, or less than weight. For example, an embodiment that is substantially free of carbon, but still includes a very small amount of carbon may include from 0.05% to 0.15% carbon. The alloy may also be free or substantially free of any other elements of the periodic table not specifically noted as present.

According to a further embodiment, the alloy comprises no more than 1%, no more than 0.5%, no more than 0.4%, no more than 0.3%, no more than 0.2%, no more than 0.1%, no more than 0.5%, or no more than 0.04% of silicon (e.g., 0-0.04% max, Si). In an embodiment, the alloy may be entirely free of silicon. The alloy may be substantially or entirely free of phosphorous and/or sulfur, as quantified above (e.g., no more than 0.04%, or no more than 0.04% max by weight of each). For example, as a trace element, if present, phosphorus may be at 0% to 0.04% max, while sulfur, if present, may be at 0% to 0.03% max. Iron may be present, or absent, in small amounts (e.g., 0% to 3% max Fe).

The radiopaque stent of the present disclosure overcomes limitations of other stents, e.g., particularly L-605 stents, which exhibit less than ideal radiopacity, without increasing tungsten content, which can result in solubility problems, as tungsten normally separates into a second phase in Co—Cr at concentrations slightly greater than 15% by weight. The present methods disclose how to ensure that the stent can be formed from a homogenous material (no coatings, no varying metallic layers, no radiopaque markers or the like), in which the alloy exhibits a substantially homogenous single-phase microstructure, even though precipitates normally form within such a composition, which precipitates are not resolved through conventional heat treatments. The presently described treatments are surprisingly capable of resolving such problems.

Such a stent imparts a more visible image when absorbing x-rays during fluoroscopy as compared to a dimensionally similar L-605 stent. With this more visible image, the entire stent is better observed by the practitioner placing the stent. The image observed by the practitioner is not "washed out" due to excessive brightness and is not too dim. Because of the improved image contrast, the stent is accurately positioned and manipulated within a lumen of a patient, with a radiopacity such that stent expansion during and after deployment may be assessed accurately by the practitioner. An additional advantage to the increased radiopacity is the visualization of the stent and the underlying vessel during follow-up examinations by the practitioner.

Because the entire stent is radiopaque, the diameter and length of the stent are readily discerned by the practitioner. Also, because the stent itself is made of the radiopaque alloy, the stent does not have problems associated with radiopaque coatings or varying metallic layers (e.g., no core/shell structure), such as cracking or separation or corrosion at interfaces inherent in such configurations. Also, because the entire stent is radiopaque, the stent does not require extra markers with their attendant issues. While some embodiments as described herein may include no such coatings or varying composition layers, or the presence of markers so as to provide such benefits, in another embodiment, it may be possible to provide a stent where at least a portion of the stent (e.g., the stent body, or a core, or a shell thereof) is formed from the alloy and processes described herein, and another portion of the stent (e.g., the other of the core or shell, or markers) are formed from a different material and/or process.

The low profile of the Co—Cr—Ni—W—Pt stent, coupled with its enhanced radiopacity renders the stent more easily deliverable with easier observation and detection throughout its therapeutic use than stents heretofore available. A stent constructed of a Co—Cr—Ni—W—Pt alloy as contemplated herein can be made thinner than one of stainless steel without sacrificing fluoroscopic visibility. The low profile of the Co—Cr—Ni—W—Pt stent renders the stent more deliverable with greater flexibility. While platinum is an exemplary material for inclusion in the present alloy in order to increase radiopacity, it will be appreciated that other radiopacifying elements with a radiopacity greater than that provided by cobalt may alternatively or additionally be used. For example, any of various platinum group metals, precious metals, or refractory metals described in applicant's U.S. Pat. Nos. 9,566,147; 10,441,445 and 11,298,251, as well as U.S. application Ser. Nos. 13/298,070; 61/414,566; 62/914,806; 17/068,526 and 17/562,592 may also benefit from the processing steps described herein, particularly where such alloy may include Co, Cr, and W (e.g., Co, Cr, Ni, W, and one or more selected radiopacifying elements). Each of the above referenced patents and applications is herein incorporated by reference in its entirety.

Furthermore, the use of a Co—Cr—Ni—W—Pt alloy that includes, e.g., 20-25% platinum by weight in a substantially homogenous (single-phase) composition results in improved radiopacity of the low profile stent of the present disclosure over prior art cobalt chromium alloys, and increases deliverability of the stent and may offer significant performance advantages regarding decreasing the fluid mechanical disturbances of blood flow. Improved radiopacity assists the practitioner in placing the device precisely. Inflation or other deployment of the stent is better monitored because the stent is better visible to the practitioner. This visibility reduces the incidence and probability of an under-deployed stent. Further, in-stent restenosis is monitored as the stent and an injected contrast agent are able to be imaged simultaneously. Unlike some stents, the stent of the present disclosure does not produce an image which is too bright, thereby obscuring imaging of the underlying vessel morphology.

While cobalt chromium alloys containing up to 15% by weight tungsten, such as L-605, have been used in many applications, these alloys have insufficient radiopacity. The composition of L-605 is as follows. Values may vary somewhat (e.g., ±1 percentage point).

TABLE 1

ASTM F90 L-605 Alloy

| Element | Weight Percent | Atomic Percent |
|---|---|---|
| Cobalt | 53.4 | 53.9 |
| Chromium | 20 | 24.4 |
| Tungsten | 15 | 5.2 |
| Nickel | 10 | 10.8 |
| Manganese (maximum) | 1.5 | 2.3 |
| Iron (maximum) | 0.1 | 3.4 |

L-605 is reported to have a melting range of 1602 to 1683K (e.g., 1329° C. to 1410° C.) a maximum hardness of 277 HB and a density of 9.13 g/cm$^3$. This alloy in annealed bar form has a minimum ultimate tensile strength of 125 ksi, a minimum yield strength of 45 ksi and a minimum total elongation of 30%. In an embodiment, the contemplated alloys may have similar tensile strength, yield strength, and elongation properties, as such properties are desirable. That said, the relative radiopacity of L-605 is lacking, e.g., being only 3.6 barnes/cc. While this is better than stainless steel (with a relative radiopacity of only about 2.5 barnes/cc), it is far below a more suitable range, such as greater than 4 barnes/cc, greater than 4.5 barnes/cc, or from 4 barnes/cc to 10 barnes/cc, 4 barnes/cc to 8 barnes/cc, or 4 barnes/cc to 7 barnes/cc.

Figure 1:
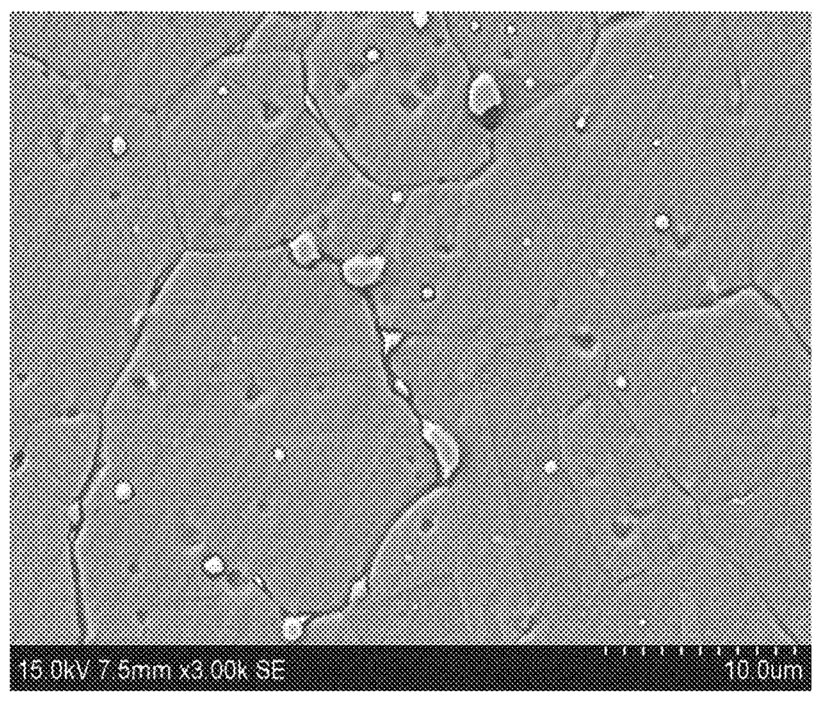
FIG. 1 is an SEM image of an exemplary cobalt-chromium-tungsten alloy, taken during tube draw, showing the presence of undesirable precipitates in the alloy structure.

As shown in FIG. 1, when initially forming an alloy based on L-605, but in which a portion of the cobalt has been replaced, so that the alloy now includes 25% by weight platinum, problems with the microstructure were observed. The manufacture of metallic alloys for use in stents includes a process of alloy formation melting in specialized furnaces to fuse the elements involved. The material then undergoes extrusion to form bars, normalization heat treatments, forging and machining to form rods suitable for tube draw.

The tube draw process involves several stages of draw through dies that reduce the tube diameter, as well as cleaning and annealing heat treatments. The annealing heat treatment re-creates the crystalline structure of the alloy and softens the material in preparation for the next stage of tube draw.

Because the "P-605" alloy differs in composition from standard L-605, the same settings for normalization, tube draw, and annealing heat treatment used for processing L-605 are not applicable. In order to develop these processes and monitor the condition of the new P-605 alloy, metallographic analysis was conducted regularly during the testing process described herein.

A significant problem was detected during such metallographic evaluations conducted during tube draw. FIG. 1 shows an example of the problematic microstructure detected, in the form of unacceptably high levels of precipitates present in the alloy, particularly at the grain boundaries, as shown. Conventional heat treatments were not able to resolve such precipitates.

As can be seen in FIG. 1, the alloy structure has an irregular appearance. The darker lines are grain boundaries were the acid used during etching has preferentially attacked material at the grain boundaries. This appears similar to voids or depressions in the material, although this is not the case in the actual alloy and such grain boundary appearance is not unusual after etching. The real problem seen in FIG. 1 is the presence of the lighter colored particles. These precipitate formations are not part of the normal desired alloy structure, but are made up of significantly harder, non-ductile particles, having a composition that differs from the much softer ductile structure of the desired homogenous alloy.

Such particles are unacceptable in materials for cardiovascular stent applications, for multiple reasons. For example, stents need to be ductile to facilitate compression onto the balloon, deployment, and to allow for minor distortion that occurs during heartbeat compression of the artery. The observed precipitate particles result in an overall structure that does not have a homogeneous crystalline structure. Experience by applicant has shown that these particles are hard ceramic-like crystalline precipitates that are not ductile, and not capable of mechanical distortion like the normal alloy structure.

Another reason that such particles are problematic is that they may be only weakly bonded into the alloy structure. It can be seen in FIG. 1 that the light colored particles are resistant to acid etch attack and appear separate or separable from the primary alloy structure.

III. Description of the Problem

Figure 2:
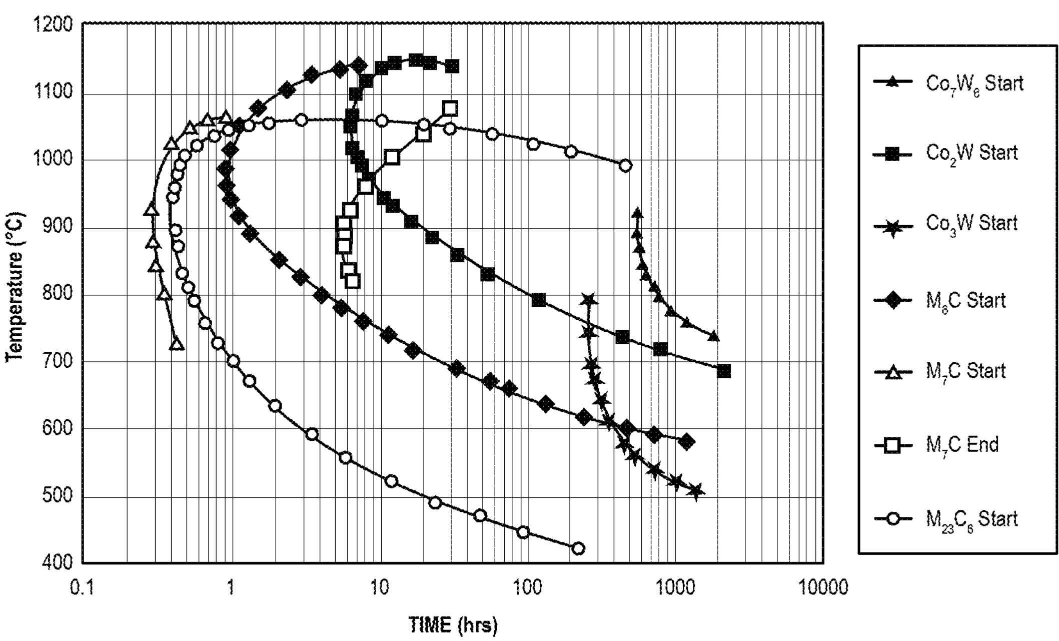
FIG. 2 is a time, temperature, transition (TTT) graph for L-605 cobalt-chromium alloy.

Typical cobalt chrome alloy manufacture is known to sometimes result in precipitate particles that appear similar to those shown in FIG. 1. Precipitate formation in solid metals during heat treatment are described by Temperature, Time, Transition (TTT) graphs, such as shown in FIG. 2, which shows an exemplary TTT chart for L-605 alloy (Julien Favre, Damien Fabregue, Eric Maire, Akihiko Chiba. Grain growth and static recrystallization kinetics in Co-20Cr-15W-10Ni (L-605) cobalt-base superalloy. Philosophical Magazine 94(18), D01:10.1080/14786435.2014.903342, herein incorporated by reference in its entirety).

FIG. 2 illustrates how precipitate formations are formed in solid metals. The Y axis shows temperature and the X axis shows time. The multiple illustrated curves refer to different stoichiometric forms of precipitates, and the conditions (time and temperature) under which such precipitates form. Many of the precipitates are various forms of ceramic-like intermetallic compounds formed from cobalt and tungsten, while others are metal carbides. For example, the "M" in FIG. 2 designates that any of various metals that are present may form such a carbide precipitate. As is the case with much scientific literature, TTT diagrams show formation conditions in ideal conditions, and real-world variability such as volume of metal, surface area ratios, and slight variations in composition may influence actual results. As such, TTT diagrams can be a guide to conditions that may result in precipitate formation, rather than an exact representation of what is occurring under real manufacturing conditions.

It is also known that the most common form of precipitate that forms in L-605 alloy is a combination of tungsten and carbon known as tungsten carbide labeled as $M_{23}C_6$ in the TTT diagram. The composition of the precipitates can be confirmed using a Scanning Electron Microscope (SEM) fitted with Energy Dispersive X-Ray Spectroscopy (EDS). EDS analysis of the particulates in new P-605 alloy showed high levels of tungsten. The fact that no high levels of other metallic elements of the alloy were detected strongly suggested that the precipitates detected are some type of tungsten carbide.

One insight that can be gleaned from a TTT diagram is determination at what temperature no precipitates should form, even if the alloy is held at such temperature for an extended period. The TTT diagram shown in FIG. 2 indicates this condition should be prevalent above 1200° C. Another key learning from the TTT of FIG. 2 is that at such elevated temperatures, any precipitates that may be present would be expected to dissolve back into the alloy structure, if held at such temperature for sufficient time for equilibrium to be reached. In summary, conventional thinking is that the formation of precipitates in the alloy structure should be resolved by heat treating to this temperature range, followed by rapid cooling of the alloy to prevent reformation of precipitates.

Tungsten has the highest meting temperature of any metal, at over 3400° C. Its atoms are large compared to other elements in L-605 so it is expected that dissipation of precipitates containing tungsten should require high temperature and long dwell times at such elevated temperature to cause the precipitates to dissolve. As noted above, the volume and surface area of the tube being treated may also be a relevant factor. For example, the relatively low cross-sectional volume and large surface area to volume ratio of such tubing allows for rapid heating and cooling of the alloy.

IV. Attempts to Resolve Precipitates in P-605 Alloy

The conventional path to resolve tungsten carbide precipitates in an L-605 alloy would be to monitor the structure over subsequent annealing stages as the precipitates gradually dissipate. At a finished tube wall thickness of 100 microns such precipitates should be dissipated during a single annealing cycle.

When attempting such conventional treatments on the P-605 alloy, it was observed that the precipitates were reduced only very slightly at each stage of annealing, and it was realized that the precipitates would not be fully dissolved before arriving at the final tube size. As noted above, the presence of such precipitates in the final alloy for use as a stent is unacceptable. As a result of this problem, the P-605 tube draw process was halted, as it was apparent that a conventional treatment process was not going to work.

A technical review was conducted, and concluded that the strategy for resolution of the precipitates was based on the TTT diagram for L-605, but that P-605 is a new alloy, that while similar to L-605, it could nevertheless exhibit TTT characteristics that would differ from L-605. The tube draw annealing process is conducted at about 1200° C. and involves rapid quench, which process is effective at resolving tungsten carbide precipitates in L-605. As described above, tungsten has a very high melting point so dissolution of such compounds with carbon would be expected to require high temperature, and significant dwell time, as tungsten atoms are slow to migrate in the Co—Cr lattice structure. The conclusion of the technical review was to try elevating the annealing temperature and increasing the dwell time at such temperature to dissolve existing tungsten rich precipitates, followed by rapid quench to prevent reformation.

To test such a proposal annealing temperatures were gradually increased from 1200° C. to 1240° C. The outcome of such processing was that the precipitates were still not resolved.

Given that the precipitates were not resolved by increasing the annealing temperature, it was determined to alter the test set up, and increase the annealing dwell time, at a series of temperatures. Table 2 below shows the various annealing times and temperatures that were attempted, as well as the outcome of such processing.

TABLE 2

| Annealing Temp. (° C.) | Annealing Time (min) | Quench Rate to 600° C. | Outcome |
|---|---|---|---|
| 1225 | 60 | <1 minute | Not Resolved |
| 1250 | 60 | <1 minute | Not Resolved |
| 1275 | 60 | <1 minute | Not Resolved |
| 1300 | 60 | <1 minute | Not Resolved, plus incipient melting |

At 1300° C. a condition known as incipient melting occurred where the lower melting point components of the alloy begin to melt out. This significantly changes the alloy crystalline structure, resulting in the formation of new alloy phases, making the resulting material unsuitable for stent material applications. Overall, the results continued to show that tungsten rich precipitates were still not being driven into solution.

The next suggestion was to use a heat treatment of as high a temperature as possible, without causing incipient melting, for further increased dwell times. Table 3 below shows the details of such additional trials, and their outcomes. As is apparent, such treatments were also not effective in resolving the presence of the observed precipitates, leaving few if any apparent options for precipitate resolution.

TABLE 3

| Annealing Temp. (° C.) | Annealing Time (min) | Quench Rate to 600° C. | Outcome |
|---|---|---|---|
| 1275 | 2 hours | <1 minute | Not Resolved |
| 1275 | 12 hours | <1 minute | Not Resolved |
| 1275 | 24 hours | <1 minute | Not Resolved |
| 1275 | 48 hours | <1 minute | Not Resolved |

Given such repeated failures, a further review was conducted, with the following team observations:

platinum was not detected in any of the unsuitable formations;

it was not understood why the addition of platinum and proportional reduction in cobalt in the L-605 Co—Cr alloy structure could alter the formation of tungsten rich particulate formations;

alloy elements have solubility ranges into the main constituents and other alloy elements—it was wondered if the solubility of tungsten in Co—Cr be changed by the presence of platinum, and therefore could the tungsten rich particles be unalloyed tungsten. Cobalt-platinum phase diagrams available in the literature show that platinum has high solubility in cobalt so this does not support the theory that platinum has altered the solubility of tungsten in Co—Cr;

composition and phases in metallic alloys are highly complex—alloy phase diagrams and studies of L-605 Co—Cr are available but references for the composition of P-605 are not available;

the tungsten rich particulate formations may either not be a precipitate or could be a formation that once generated, subsequent heat treatment cannot resolve;

such formations could have occurred during metal processing prior to tube draw;

it was wondered if the resolution heat treatments used may have created the conditions for a tungsten rich phase to evolve during further heat treatments;

knowledge of L-605 phase diagrams, face centered atomic structure, and alloy TTT diagrams may not apply to P-605 alloy; and at this point, the team was not able to identify a resolution path forward.

Before giving up on the project, it was decided to collate all information gathered to date, review all as-cast and metal processing microstructural data available, go back to basic review of all literature references available, and if still no path forward could be identified, the project would be abandoned.

V. Resolution

Figure 3:
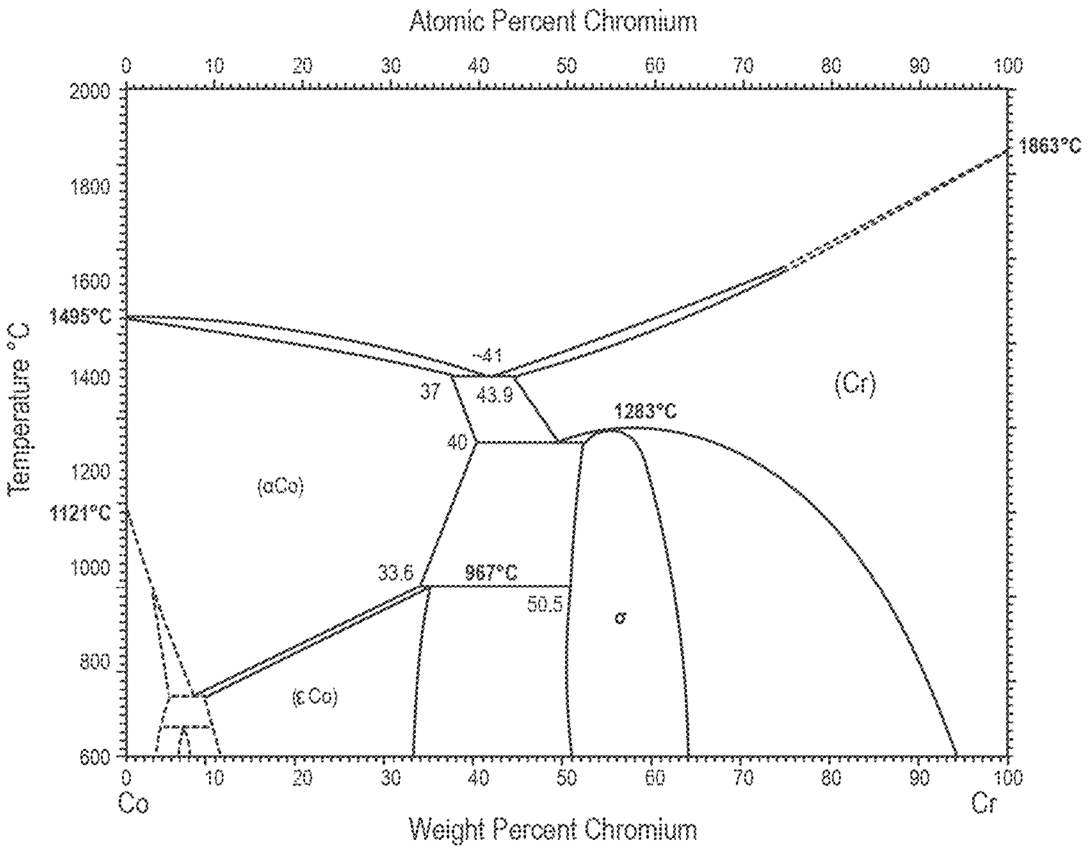
FIG. 3 shows a binary phase diagram for cobalt-chromium.

The team consensus was that the microstructure of P-605 is much more complex than illustrated by available TTT diagrams. For example the phase diagram for Co—Cr shows several atomic crystalline structures that exist according to temperature and processing conditions, as shown in FIG. 3. The Co—Cr phase diagram of FIG. 3 illustrates the crystal phases that exist with increasing proportion of chromium in a pure cobalt-chromium alloy. L-605 contains 18% to 22% chromium, and the important phase structure needed for flexibility of stent materials is shown as αCo in the phase diagram of FIG. 3. Of course the utility of FIG. 3 is limited, as L-605 and P-605 alloys contain several other alloying elements such as nickel, tungsten, manganese, (and platinum in the case of P-605) in addition to chromium. In other words, neither L-605 nor P-605 alloys are simple binary alloys, such as that of FIG. 3.

Several other forms of crystalline phase and intermetallic compounds can exist in an alloy and a significant problem for P-605 is that no phase diagrams, or identification of intermetallic compound structures that might form are available. Creating such information would take several years, for suitably trained post PhD graduates.

After reviewing the available data and literature, applicant theorized that $Co_3W$ (an intermetallic compound) could potentially be the material from which the precipitates seen in FIG. 1 were formed. For example, although EDS analysis of the precipitates showed high tungsten content, it also showed the presence of trace cobalt. Particular features of this intermetallic compound include very high stability, and a tendency for this material to gradually form over time. It was observed that the previous attempts to dissipate the tungsten rich compound focused on high temperature and extended time believing that this was needed for tungsten to migrate, and cause the precipitate to dissolve. It was further theorized that these conditions may actually promote formation and stability of a $Co_3W$ intermetallic compound, so that the extended time approach would not resolve the issue. Even though the data shown in FIG. 2 shows that $Co_3W$ does not form at temperatures over about 800° C. in L-605, the different observed results may be due to the alloy being P-605, or other unpredictable factors.

Figure 4:
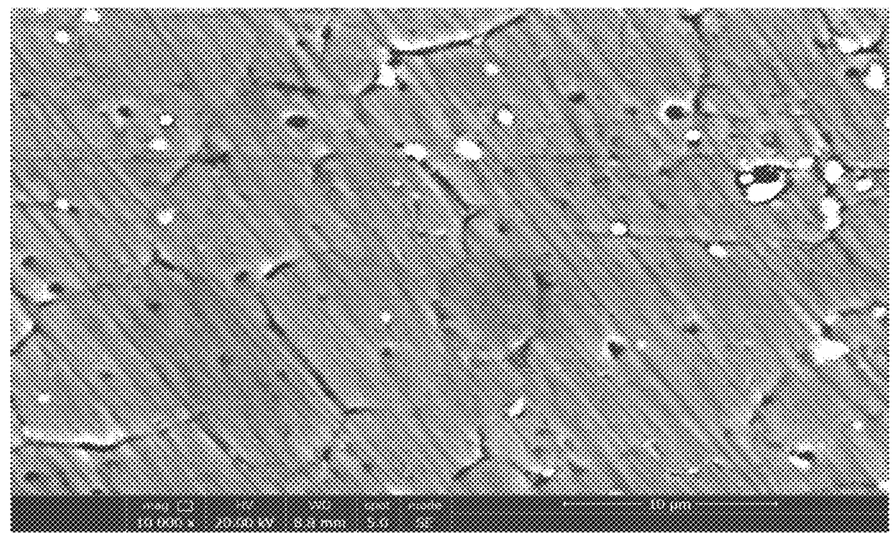
FIG. 4 is an SEM image of a similar cobalt-chromium-tungsten alloy as shown in FIG. 1, before a heat treatment according to the present disclosure, showing undesirable precipitates.
Figure 5:
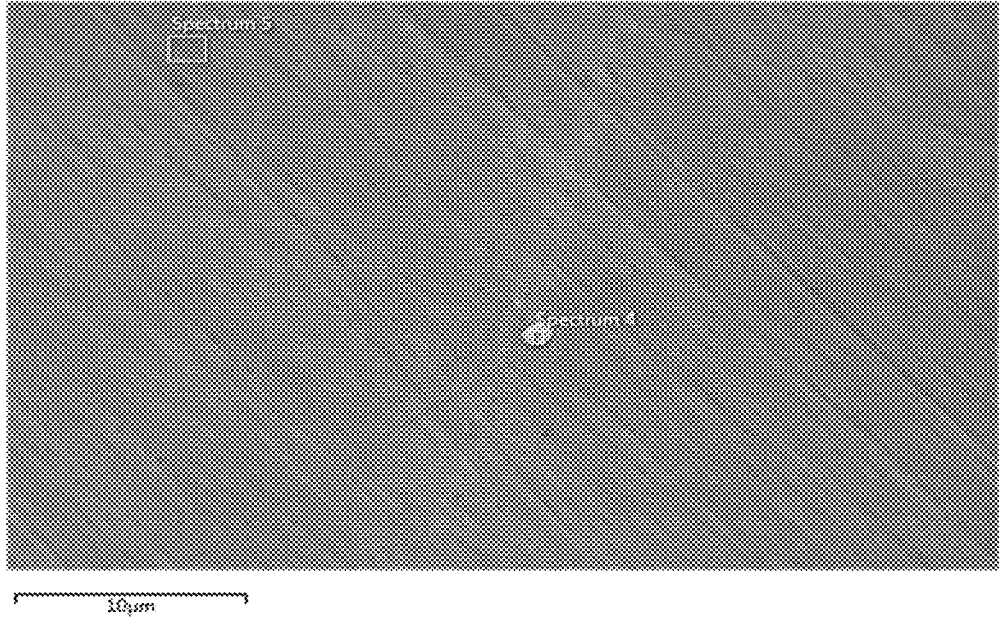
FIG. 5 is an SEM image of the alloy of FIG. 4, after the heat treatment according to the present disclosure, where the undesirable precipitates have been substantially removed.

It was decided to conduct a further set of heat treatment trials and include a shorter hold time, of only 30 minutes, at 1250° C. This produced dramatically different results than those described above, even compared to the similar treatment of 1250° C. for 60 minutes. The pre-treatment structure, including significant precipitates, is shown in FIG. 4. This microstructure is very similar to that shown in FIG. 1. FIG. 5 shows the resulting microstructure of the same material shown in FIG. 4, after treatment at 1250° C. for 30 minutes. As can be seen, the structure of the alloy has completely changed and the degree of intermetallic compound has been dramatically reduced, disappearing almost completely. EDS analysis showed this to be a tungsten rich particle similar to the originally detected particles. The size of the detected particle (labeled "spectrum 4" in FIG. 5) was around 3 μm or less. This result eliminated the theory that tungsten solubility was the cause of the observed precipitation. It is also apparent from FIG. 5 that grain boundary appearance has also dramatically changed, showing a much more uniform composition within the alloy.

The results are surprising, as the solution that actually worked to resolve the precipitate particles is counterintuitive, and does not align with standard metallurgical theory and practice, which recognizes tungsten as a high melting point element that requires high energy to disassociate from bonds and which is slow to migrate (hence the understanding that very high temperatures and long treatment times should be more effective in resolving such particulates). None of the metallurgical members of the team have observed this form of material structural alteration, or would have predicted its success, using a heat treatment at 1250° C. for 30 minutes, followed by a rapid quench, particularly where the same temperature and rapid quench, held for 60 minutes was shown to be completely ineffective.

The conclusion was that the alloy material of FIG. 5 can be processed to the desired final tube condition, and that such alloy material as shown in FIG. 5 will be suitable for processing into final condition manufacture and testing of stents.

From the results and data, it is apparent that in an embodiment of the present invention the rapid quench may be performed within a period of time of less than 5 minutes, less than 3 minutes, less than 2 minutes, or less than 1 minute. The rapid quench may be performed by immersing the alloy in water.

In an embodiment, the alloy comprises cobalt, in an amount of from 20% to 40% by weight.

In an embodiment, the alloy comprises chromium in an amount of about 20% by weight.

In an embodiment, the alloy comprises nickel in an amount of about 10% by weight.

In an embodiment, the alloy is substantially or entirely free of molybdenum.

In an embodiment, the alloy is substantially or entirely free of carbon.

In an embodiment, the alloy comprises no more than 1% by weight of each of silicon, phosphorus, and/or sulfur.

In an embodiment, the alloy comprises manganese in an amount of up to 5% by weight.

In an embodiment, the alloy comprises both manganese and iron in an amount of up to about 3% each, by weight.

In an embodiment, the sum of cobalt and platinum comprises from about 48% to about 60%, or 50% to 57% (e.g., about 55%) by weight of the alloy.

In an embodiment, the alloy comprises:

about 20-37% cobalt;
about 20-30% platinum;
about 19-21% chromium;
about 14-16% tungsten;
about 9-11% nickel; and
about 1-2% manganese.

In an embodiment, the alloy further comprises one or more trace elements as follows:

iron;
sulfur;
phosphorus; and
silicon.

In an embodiment, the precipitate inclusions comprise tungsten (e.g., a majority tungsten, e.g., where cobalt may also be present). In an embodiment, the precipitate inclusions comprise $Co_3W$.

In an embodiment, the alloy may be heated to about 1250° C. for a period of time that is less than 60 minutes, less than 50 minutes, no more than 45 minutes, no more than 40 minutes, such as about 30 minutes. The period of time may be at least 10 minutes, at least 15 minutes, or at least 20 minutes, such as 20-40 minutes. The temperature to which such heating may occur may be 1275° C. or less, at least 1200° C., at least 1225° C., such as 1230° C. to 1270° C., 1240° C. to 1260° C., such as about 1250° C.

The alloy is rapidly cooled from the above noted temperature, to 600° C. or less, within less than 1 minute. Such may be achieved within a water quench bath (e.g., immersing the alloy after treatment at the above temperature and hold time). Rapid cooling of the alloy may aid in maintaining the desired substantially homogenous structure seen in FIG. 5.

It can be important to not substitute any of the 10% by weight nickel content already present in a comparative L-605 alloy. For example, nickel suppresses cobalt's allotropic transformation from a face-centered-cubic ("FCC") crystal structure (where it is stable at high temperatures) to a hexagonal-close-packed ("HCP") structure (where it is stable at low temperatures). In pure cobalt, this transformation naturally occurs at around 422° C. The addition of nickel significantly reduces cobalt's transformation temperature, thereby favoring the FCC structure, which in general, is a more ductile and more creep-resistant crystal structure than HCP. The rapid cooling of the alloy solution serves to trap the cobalt in the favored FCC structure, minimizing or eliminating formation of any substantial amounts of HCP structure.

While existing processing methods for some L-605 or similar materials may generally adapt some temperature considerations to balance control of carbide formation in the alloy material with the desired mechanical properties of the final material, up to now, no consideration has been given to the processing that would be required to maintain a primarily single-phase, FCC microstructure in a Co—Cr—Ni—W—Pt alloy with 20-30 weight percent platinum, e.g., paired with other compositional characteristics as described herein. As some embodiments of the current Co—Cr—Ni—W—Pt alloys may be substantially or entirely free of carbon, the temperatures and cooling times of the processing described herein may be directly focused on the resolution of tungsten rich precipitates that may otherwise form, to achieve a substantially homogenous, single-phase, FCC microstructure, rather than any considerations related to potential carbide formation, or other purposes.

While iron and/or manganese may be present, they each may represent no more than 3%, or no more than 2% (e.g., 1.5% by weight) of the alloy. The alloy may also be free, or substantially free of other elements of the periodic table not specifically listed in exemplary alloys described herein.

The resulting alloys are advantageously stable and may be compatible with additional heat treatments, such as age hardening, without disturbing the desired substantially homogenous microstructure shown in FIG. 5. For example, subsequent age hardening treatments may include heating the alloy to 600 to 1000° C., 600 to 800° C., or 600 to 675° C. for at least about 1 hour, at least about 4 hours, at least about 8 hours, at least about 16 hours, from 1 hour to 256 hours, or from 1 hour to 16 hours. Aging for the described time periods at the described temperatures may aid ensuring that any $Co_3W$ particulates still present exhibit very small grain or particle sizes. The austenitic stabilization of the material advantageously prevents significant formation of HCP structure. The age hardening can be configured to impart a particular yield strength to the material, according to the intended use, without affecting radiopacity.

By way of example, by "substantially homogenous", it may be meant that any secondary phase is limited to no more than 10% volume fraction, no more than 5% volume fraction, no more than 3% volume fraction, no more than 2% volume fraction, or no more than 1% volume fraction. Any present second phase further may be well dispersed, e.g., having a maximum or even average particle size of no more than 5 μm, such as from 0.5 μm to 5 μm. An example of such a substantially homogenous structure is shown in FIG. 5. In one embodiment, the alloy of the current disclosure may have a yield strength of at least 45 ksi (310 MPa).

For some embodiments, the radiopaque stent of the present disclosure is fabricated from a single tube of Co—Cr—Ni—W—Pt alloy subjected to chemical etching, laser machining, conventional machining, electronic discharge machining (EDM), ion milling, slurry jet, or electron beam treatment or combinations of these treatments. For other embodiments, the stent is fabricated from wire elements of Co—Cr—Ni—W—Pt alloy that are welded together. For additional embodiments, the stent is fabricated from flat stock and is patterned, then rolled and welded. For other embodiments, the stent is fabricated from near-net shape processing such as metal injection molding.

Exemplary alloy compositions are shown below.

Example 1

| Symbol | Name | Weight % |
|---|---|---|
| Si | Silicon | 0-0.04 |
| P | Phosphorous | 0-0.04 |
| Si | Sulfur | 0-0.03 |
| Cr | Chromium | 19-21 |
| Mn | Manganese | 1-2 |
| Fe | Iron | 0-3 |
| Co | Cobalt | 20-37 |
| Ni | Nickel | 9-11 |
| W | Tungsten | 14-16 |
| Pt | Platinum | 20-30 |
| | Total | 100.00 |

Example 2

| Symbol | Name | Weight % |
|---|---|---|
| Si | Silicon | 0-0.04 |
| P | Phosphorous | 0-0.04 |
| Si | Sulfur | 0-0.03 |
| Cr | Chromium | 20 |
| Mn | Manganese | 1.5 |
| Fe | Iron | 0-3 |
| Co | Cobalt | 33.5 |
| Ni | Nickel | 10 |
| W | Tungsten | 15 |
| Pt | Platinum | 20 |
| | Total | 100.00 |

Example 3

| Symbol | Name | Weight % |
|---|---|---|
| Si | Silicon | 0-0.04 |
| P | Phosphorous | 0-0.04 |
| Si | Sulfur | 0-0.03 |
| Cr | Chromium | 20 |
| Mn | Manganese | 1.5 |
| Fe | Iron | 0-3 |
| Co | Cobalt | 28.5 |
| Ni | Nickel | 10 |
| W | Tungsten | 15 |
| Pt | Platinum | 25 |
| | Total | 100.00 |

Example 4

| Symbol | Name | Weight % |
|---|---|---|
| Si | Silicon | 0-0.04 |
| P | Phosphorous | 0-0.04 |
| Si | Sulfur | 0-0.03 |
| Cr | Chromium | 20 |
| Mn | Manganese | 1.5 |
| Fe | Iron | 0-3 |
| Co | Cobalt | 23.5 |

-continued

| Symbol | Name | Weight % |
|---|---|---|
| Ni | Nickel | 10 |
| W | Tungsten | 15 |
| Pt | Platinum | 30 |
| | Total | 100.00 |

As shown above, in an example, the alloy may consist essentially of Co, Cr, Ni, W, and Pt, where any additional elements that may be present, may be present at less than 2% by weight (e.g., particularly in the case of Mn and/or Fe), less than 1%, or less than 0.5%, or less than 0.25% (e.g., particularly in the case of Si, P, and/or S), if at all.

Figure 6:
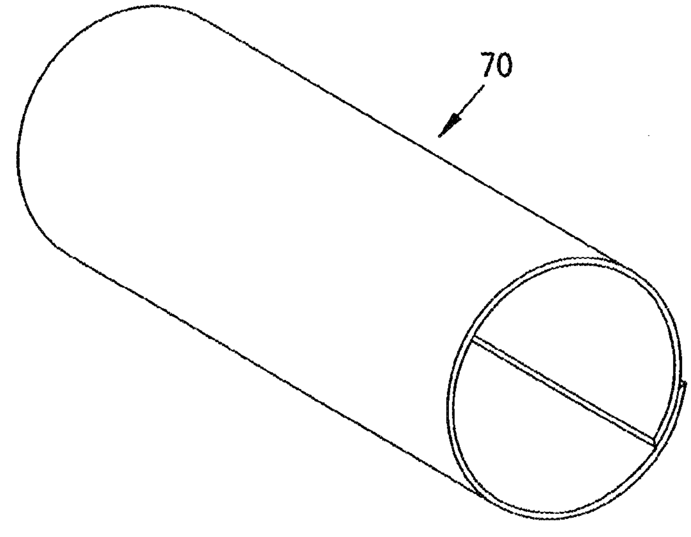
FIG. 6 is a perspective view of a tubular embodiment of a radiopaque stent of that can be formed according to the present invention.
Figure 7:
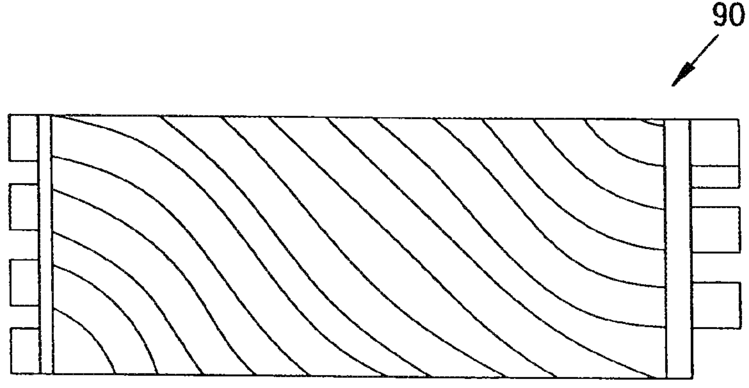
FIG. 7 is a side view of a coiled configuration of a radiopaque stent that can be formed according to the present invention.
Figure 8:
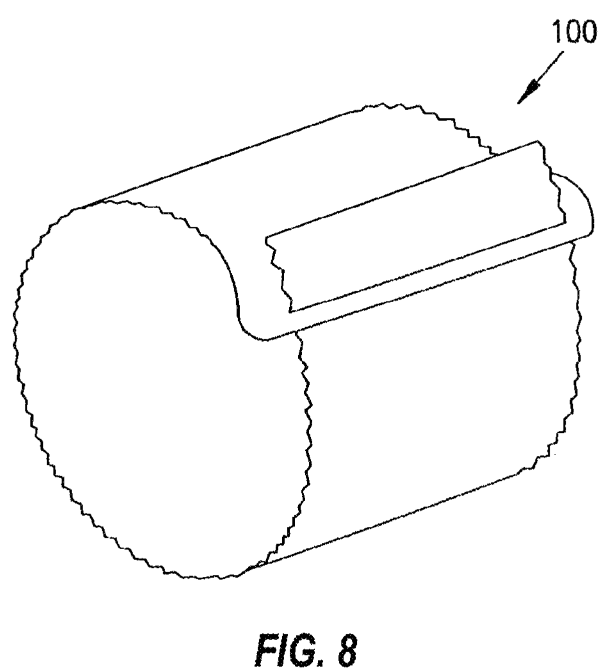
FIG. 8 is a perspective view of a ratcheted configuration of a radiopaque stent that can be formed according to the present invention.
Figures 9, 10:
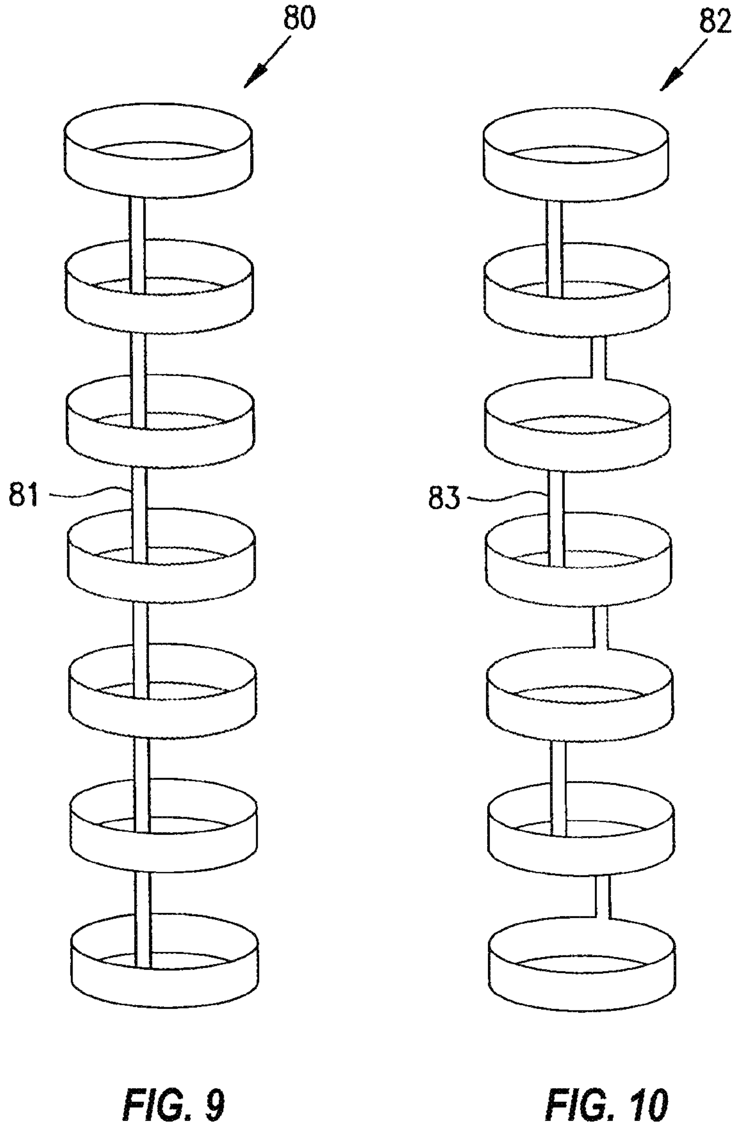
FIG. 9 is a perspective view of a configuration of a radiopaque stent that includes a backbone that can be formed according to the present invention.
FIG. 10 is a perspective view of another configuration of a radiopaque stent that includes a staggered backbone that can be formed according to the present invention.
Figure 11:
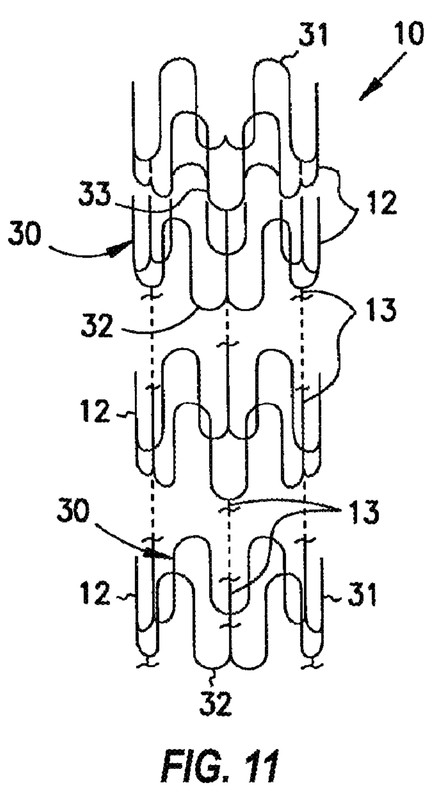
FIG. 11 is a perspective view of a configuration of a radiopaque stent that can be formed according to the present invention, in an unexpanded state, with one end of the stent being shown in an exploded view to illustrate the details thereof.

The radiopaque stent of the present disclosure may be fabricated according to any number of configurations. Non-limiting exemplary configurations include a solid cylinder, illustrated at 70 in FIG. 6, a coiled stent illustrated at 90 in FIG. 7, a ratcheting stent 100, illustrated in FIG. 8, a stent embodiment 80 with a backbone 81, illustrated in FIG. 9 or a stent embodiment 82 with a staggered backbone, illustrated in FIG. 10. Additional configurations are shown in FIGS. 11-12. In an embodiment, the entirety of the stent body may be formed from the radiopaque Co—Cr alloy described herein (e.g., without various metallic layers, markers, or the like).

One type of radiopaque stent design embodiment is a high precision patterned cylindrical device. An example of such is illustrated generally at 10 in FIG. 13. The stent 10 typically comprises a plurality of radially expanded cylindrical elements 12 disposed generally coaxially and interconnected by elements 13 disposed between adjacent cylindrical elements.

For some embodiments, the stent 10 is expanded by a delivery catheter 11. The delivery catheter 11 has an expandable portion or a balloon 14 for expanding of the stent 10 within an artery 15. The delivery catheter 11 onto which the stent 10 is mounted is similar to a conventional balloon dilation catheter used for angioplasty procedures. The artery 15, as shown in FIG. 13, has a dissected lining 16 which has occluded a portion of the arterial passageway.

Each radially expandable cylindrical element 12 of the radiopaque stent 10 is independently expandable. Therefore, the balloon 14 may be provided with an inflated shape other than cylindrical, e.g., tapered, to facilitate implantation of the stent 10 in a variety of body lumen shapes.

The delivery of the radiopaque stent 10 is accomplished by mounting the stent 10 onto the inflatable balloon 14 on the distal extremity of the delivery catheter 11. The catheter-stent assembly is introduced within the patient's vasculature using conventional techniques through a guiding catheter which is not shown. A guidewire 18 is disposed across the damaged arterial section and then the catheter-stent assembly is advanced over a guidewire 18 within the artery 15 until the stent 10 is directly under detached lining 16 of the damaged arterial section. The balloon 14 of the catheter is expanded, expanding the stent 10 against the artery 15, which is illustrated in FIG. 14. While not shown in the drawing, the artery 15 is preferably expanded slightly by the expansion of the stent 10 to seat or otherwise fix the stent 10 to prevent movement. In some circumstances during the treatment of a stenotic portion of an artery, the artery may have to be expanded considerably in order to facilitate passage of blood or other fluid therethrough. This expansion is easily observable by the interventionalist with the radiopaque stent of the present disclosure. While balloon expandable stents are described, it will be appreciated that the alloys and configurations described herein may, in at least some embodiments, be self-expanding.

The stent 10 serves to hold open the artery 15 after the catheter 11 is withdrawn, as illustrated in FIG. 15. Due to the formation of the stent 10 from the elongated tubular member, the undulating component of the cylindrical elements of the stent 10 is relatively flat in transverse cross section so that when the stent is expanded, the cylindrical elements are pressed into the wall of the artery 15 and as a result do not interfere with the blood flow through the artery 15. The cylindrical elements 12 of the stent 10 which are pressed into the wall of the artery 15 are eventually covered with endothelial cell growth which further minimizes blood flow interference. The undulating pattern of the cylindrical sections 12 provides good characteristics to prevent stent movement within the artery. Furthermore, the closely spaced cylindrical elements at regular intervals provide uniform support for the wall of the artery 15, and consequently are well adapted to tack up and hold in place small flaps or dissections in the wall of the artery 15 as illustrated in FIG. 14 and FIG. 15. The undulating pattern of the radiopaque stent is readily discernable to the interventionalist performing the procedure.

FIG. 11 is an enlarged perspective view of the stent 10 shown in FIG. 13 with one end of the stent shown in an exploded view to illustrate in greater detail the placement of interconnected elements 13 between adjacent radially expandable cylindrical elements 12. Each pair of interconnecting elements 13 on one side of the cylindrical element 12 are positioned to achieve maximum flexibility for the stent 10. In an embodiment shown in FIG. 11, the stent 10 has three interconnecting elements 13 between adjacent radially expandable cylindrical elements 12 which are 120 degrees apart. Each pair of interconnecting elements 13 on one side of a cylindrical element 12 are offset radially 60 degrees from the pair on the other side of the cylindrical element. The alternation of the interconnecting elements results in a stent which is longitudinally flexible in essentially all directions. Various configurations for the placement of interconnecting elements are possible. However, as previously mentioned, all of the interconnecting elements of an individual stent are secured to either the peaks or valleys of the undulating structural elements in order to prevent shortening of the stent during the expansion thereof.

The number of undulations may be varied to accommodate placement of interconnecting elements 13, e.g., at the peaks of the undulations or along the sides of the undulations as shown in FIG. 12.

As best observed in FIG. 11 and FIG. 12, cylindrical elements 12 are in the form of a serpentine pattern 30. As previously mentioned, each cylindrical element 12 is connected by interconnecting elements 13. Serpentine pattern 30 is made up of a plurality of U-shaped members 31, W-shaped members 32 and Y-shaped members 33, each having a different radius so that expansion forces are more evenly distributed over the various embodiments.

The illustrative stent 10 and other stent structures can be made using several techniques, including laser machining. One method of making the radiopaque stent is to cut a thin walled tubular member made of the radiopaque Co—Cr—Ni—W—Pt alloy described herein, to remove portions of the tubing in a desired pattern for the stent, leaving relatively untouched the portions of the radiopaque Co—Cr—Ni—W—Pt alloy tubing which are to form the stent. In accordance with one method of making the device of the present disclosure, the tubing is cut in a desired pattern using a machine-controlled laser as illustrated schematically in FIG. 16.

Typically, before crimping, the stent has an outer diameter on the order of about 0.04 to 0.10 inches in the unexpanded condition, approximately the same outer diameter of the tubing from which it is made, and may be expanded to an outer diameter in a range of about 1 to 15 millimeters. Stents for peripheral and other larger vessels may be constructed from larger diameter tubing. The strut thickness in a radial direction is in a range of 0.001 to 0.01 inches.

Referring to FIG. 16, in one fabrication embodiment, the tubing 21 is put in a rotatable collet fixture 22, of a machine controlled apparatus 23 for positioning the tubing 21 relative to a laser 24. According to machine-encoded instructions, the tubing 21 is rotated and moved longitudinally relative to the laser 24 which is also machine controlled. The laser selectively removes the material from the tubing by ablation and a pattern is cut into the tube. The tube is therefore cut into the discrete pattern of the finished stent.

The process for cutting a pattern for the stent into the tubing may be automated except for loading and unloading the length of tubing. Referring again to FIG. 16, it may be done, for example, using a CNC opposing collet fixture 22 for axial rotation of the length of tubing. In conjunction with a CNC X-Y table 25 to move the length of tubing axially relatively to a machine-controlled laser as described. The entire space between collets is patterned using a laser setup of the foregoing example. The program for control of the apparatus is dependent on the particular configuration used.

The tubes are made of a Co—Cr—Ni—W—Pt alloy as described herein that includes significant platinum content (e.g., 20-30% platinum by weight), while maintaining primarily single-phase characteristics within the alloy. The tubes have an outside diameter of 0.04 inches to 0.10 inches and a wall thickness of 0.001 inches to 0.010 inches. In one embodiment, the tubes are fixed under a laser and are positioned using a CNC to generate a very intricate and precise pattern. Due to the thin wall and the small geometry of the stent pattern, it is necessary to have very precise control of the laser, its power level, the focus spot size and the precise positioning of the laser cutting path.

One reason to have precise control of the laser operating parameters is to minimize heat input into the stent structure, which prevents thermal distortion, uncontrolled burnout of the metal, and metallurgical damage from excessive heat. It can also be important to minimize or otherwise control heating of the stent structure which might undesirably alter the desired substantially single-phase structure, particularly given the tendency for the present alloys to form tungsten rich precipitate secondary phases. With such lasers, it is possible to make a smooth, narrow cut in the Co—Cr—Ni—W—Pt alloy tubes in very fine geometries without damaging the narrow struts that make up the stent structure, and without undesirably altering the phase characteristics. The system of the present disclosure using such lasers and their available parameter adjustments, makes it possible to cut using a narrow beam which minimizes the heat input into the material.

The positioning of the cylindrical radiopaque Co—Cr—Ni—W—Pt alloy structure benefits from use of precision CNC equipment. In addition, for some embodiments, a rotary mechanism can be provided that allows the computer program to be written as if the pattern were being cut from a flat sheet. This allows both circular and linear interpolation to be used in programming.

The optical system which expands the original laser beam delivers the beam through a viewing head and focuses the beam onto the surface of the tube, may include a coaxial gas jet and nozzle that helps remove debris from the cut face and cools the region where the beam interacts with the material as the beam cuts and vaporizes the metal. Such is also advantageous to block the beam as it cuts the top surface of the tube and prevent the beam, along with the molten metal and debris from the cut, from impinging on the opposite surface of the tube.

In addition to the laser and the CNC positioning equipment, the optical delivery system can include a beam expander to increase the laser beam diameter, a circular polarizer, typically in the form of a quarter wave plate, to eliminate polarization effects in metal cutting, provisions for a spatial filter, a binocular viewing head and focusing lens, and a coaxial gas jet that provides for the introduction of a gas stream which surrounds the focus beam and is directed along the beam axes.

The cutting process typically uses an assist gas with the laser beam, resulting in a narrow cut area and minimal molten slag along the cut. In order to remove the slag debris from the cut allowing the scrap to be removed from the remaining stent pattern, the cut tube can be soaked in an appropriate solution of mineral acids. Before it is soaked, the tube may be ultrasonically cleaned in a mineral acid solution after cutting.

Direct laser cutting produces edges which are essentially perpendicular to the axes of the laser cutting beam in contrast with chemical etching and the like which may produce patterned edges which are angled. Hence, the laser cutting process essentially provides stent cross sections from cut-to-cut which are square or rectangular. As depicted, cylindrical elements 12 are comprised of struts 30 which have generally rectangular cross sections 32 wherein the stent is laser cut from a tubular member. The struts have generally perpendicular edges 31 formed by the laser cut. The resulting stent structure provides superior performance. That said, it is possible to form stents according to the present disclosure using techniques other than laser cutting, while still providing benefits associated with the enhanced radiopacity, primarily single-phase alloy while substantially eliminating the presence of secondary phase tungsten rich precipitates, as described herein.

In other embodiments, the radiopaque Co—Cr—Ni—W—Pt alloy stent of the present disclosure is fabricated of radiopaque Co—Cr—Ni—W—Pt alloy wire elements. In another embodiment, the stent is made of a radiopaque Co—Cr—Ni—W—Pt alloy flat stock. In another embodiment, the stent is made of radiopaque Co—Cr—Ni—W—Pt alloy materials using near-net shape processing such as metal injection molding.

When expanded, the stent may cover about 10-45% of an arterial wall surface area. The radiopaque Co—Cr—Ni—W—Pt alloy stent of the present disclosure can withstand at least about 30% tensile deformation before failure.

In addition, unless otherwise indicated, numbers expressing quantities, constituents, distances, or other measurements used in the specification and claims are to be understood as optionally being modified by the term “about” or its synonyms. When the terms “about,” “approximately,” “substantially,” or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition.

As used herein, the term "between" includes any referenced endpoints. For example, "between 2 and 10" includes both 2 and 10.

Although described principally for use in manufacturing stents, it will be understood that any of the disclosed alloys and processes may also be used in the manufacture of other devices, such as medical devices, including, but not limited to guide wires, guide wire tip coils, balloon markers, balloon expandable valves, or other structures associated with catheter use, and other implantable structures in which improved radiopacity would be desirable.

The present invention can be embodied in other specific forms without departing from its spirit or essential characteristics. Thus, the described implementations are to be considered in all respects only as illustrative and not restrictive. The scope of the invention is, therefore, indicated by the appended claims rather than by the foregoing description. All changes that come within the meaning and range of equivalency of the claims are to be embraced within their scope.

The invention claimed is:

1. A process comprising:

providing an alloy formed from cobalt in an amount from about 20% to about 40% by weight, chromium, tungsten, and at least one of a platinum group metal, a precious metal, a refractory metal or another metal having an atomic number or density greater than that of cobalt; and heating the alloy to a temperature of at least 1200° C.; and quenching the alloy to 600° C. or less.

2. The process of claim 1, wherein the alloy comprises cobalt, chromium, tungsten, and platinum.

3. The process of claim 1, wherein the quenching is performed within a period of time of less than 5 minutes.

4. The process of claim 1, wherein the quenching is performed by immersing the alloy in water.

5. The process of claim 1, wherein heating the alloy is to a temperature of at least about 1250° C. for a time period of at least about 30 minutes.

6. The process of claim 1, wherein the alloy comprises chromium in an amount of about 20% by weight.

7. The process of claim 1, wherein the alloy comprises nickel in an amount of about 10% by weight.

8. The process of claim 1, wherein the alloy is substantially or entirely free of molybdenum and/or carbon.

9. The process of claim 1, wherein the quenching is performed within a period of time of less than 1 minute.

10. The process of claim 1, wherein the alloy comprises no more than 1% of each of silicon, phosphorus, and sulfur by weight.

11. The process of claim 1, wherein the alloy further comprises manganese in an amount of up to 5% by weight.

12. The process of claim 1, wherein the alloy further comprises iron in an amount of up to 5% by weight.

13. The process of claim 1, wherein the alloy further comprises both manganese and iron in a concentration of up to about 3% each, by weight.

14. The process of claim 1, wherein a sum of cobalt and platinum comprises from 48% to about 60% by weight of the alloy.

15. The process of claim 1, wherein the alloy comprises:

about 20-37% cobalt;
about 20-30% platinum;
about 19-21% chromium;
about 14-16% tungsten;
about 9-11% nickel; and
about 1-2% manganese.

16. The process of claim 15, wherein the alloy comprises one or more trace elements as follows:

0-3% iron;
0-0.03% sulfur;
0-0.04% phosphorus; and
0-0.04% silicon.

17. A process for the production of a cobalt-chromium alloy including tungsten and platinum, the process comprising:

providing an alloy formed from cobalt, chromium, tungsten, and platinum, wherein the alloy includes precipitate inclusions, so as to not be substantially homogenous;

heating the alloy to a temperature from about 1225° C. to 1275° C. for a time period from about 20 to about 40 minutes to remove the precipitate inclusions from the alloy, providing a substantially homogenous alloy; and quenching the alloy to 600° C. or less within 5 minutes.

18. The process of claim 17, wherein the precipitate inclusions comprise tungsten.

19. The process of claim 17, wherein the precipitate inclusions comprise $Co_3W$.

20. A process for the production of a stent formed from a cobalt-chromium alloy including tungsten and platinum, the process comprising:

providing an alloy in the form of a tube or a rod formed from cobalt, chromium, tungsten, and platinum, wherein the alloy includes precipitate inclusions, so as to not be substantially homogenous;

heating the alloy to a temperature from about 1225° C. to 1275° C. for a time period from about 20 to about 40 minutes to remove the precipitate inclusions from the alloy, providing a substantially homogenous alloy;

quenching the alloy to 600° C. or less within 5 minutes; and drawing the tube or rod.

* * * * *